(12) United States Patent
Couchot et al.

(10) Patent No.: US 12,384,949 B2
(45) Date of Patent: Aug. 12, 2025

(54) DROP-IN RECYCLED REFRIGERANT COMPOSITIONS HAVING LOW NET GWP REPLACING R-454B

(71) Applicant: The Coulan Company, L.L.C., Clayton, NC (US)

(72) Inventors: David L. Couchot, Mason, OH (US); Abiral Mainali, Raleigh, NC (US); Raymond E. Maloney, Clayton, NC (US)

(73) Assignee: The Coulan Company, L.L.C., Clayton, NC (US)

( * ) Notice: Subject to any disclaimer, the term of this patent is extended or adjusted under 35 U.S.C. 154(b) by 0 days.

(21) Appl. No.: 18/430,965

(22) Filed: Feb. 2, 2024

(65) Prior Publication Data
US 2024/0294817 A1 Sep. 5, 2024

Related U.S. Application Data

(62) Division of application No. 18/172,672, filed on Feb. 22, 2023.

(51) Int. Cl.
*C09K 5/04* (2006.01)
*C07C 17/383* (2006.01)

(52) U.S. Cl.
CPC ............ *C09K 5/045* (2013.01); *C07C 17/383* (2013.01); *C09K 2205/106* (2013.01); *C09K 2205/122* (2013.01); *C09K 2205/126* (2013.01)

(58) Field of Classification Search
CPC ..... C07C 17/38; C07C 17/383; C07C 17/386; C09K 5/04; C09K 5/041; C09K 5/044; C09K 5/045; C09K 2205/122; C09K 2205/32; C09K 2205/24; C09K 2205/40
See application file for complete search history.

(56) References Cited

U.S. PATENT DOCUMENTS

| 4,978,467 | A | * | 12/1990 | Shankland | ............ | C09K 5/045 |
| | | | | | | 252/364 |
| 5,616,276 | A | * | 4/1997 | Bivens | .................... | C09K 5/045 |
| | | | | | | 510/410 |
| 7,371,309 | B2 | * | 5/2008 | Boehmer | ............... | C07C 17/386 |
| | | | | | | 203/67 |

(Continued)

FOREIGN PATENT DOCUMENTS

WO    WO-02076915 A2 * 10/2002 ........... C07C 17/386

*Primary Examiner* — Matthew R Diaz
(74) *Attorney, Agent, or Firm* — Robert Goozner

(57) ABSTRACT

A refrigerant composition is made up of approximately 72-74% difluoromethane, 7-8% pentafluoroethane, 1-3% carbon dioxide, and 17-19% 1,3,3,3-tetrafluoropropene. This mixture is formed from recycled difluoromethane and pentafluoroethane, which have a net global warming potential of 0. The method of preparing this refrigerant involves injecting a mixture of recovered refrigerants, including difluoromethane, pentafluoroethane, and chlorodifluoromethane, into the center of a distillation column. The top of the column yields a refrigerant composition of 90-92% difluoromethane and 8-10% pentafluoroethane. Chlorodifluoromethane is removed from the bottom of the column. This refrigerant composition is used to create a low global warming potential refrigerant that can be used as a drop-in replacement for R-454B.

19 Claims, 16 Drawing Sheets

(56) References Cited

U.S. PATENT DOCUMENTS

| | | | |
|---|---|---|---|
| 8,075,742 B2 * | 12/2011 | Tarancon, III | C07C 17/383 203/84 |
| 2014/0222699 A1 * | 8/2014 | Low | C09K 5/045 516/8 |

* cited by examiner

ODS Refrigerant Reclamation Totals by Year (pounds)

| | CFC-11 | CFC-12 | CFC-13 | CFC-113 | CFC-114 | R-502 | HCFC-22 | HCFC-123 | HCFC-124 | R-500 | R-503 | Total |
|---|---|---|---|---|---|---|---|---|---|---|---|---|
| 2000 | 1,548,734 | 1,679,526 | 1,978 | 229,954 | 182,544 | 619,579 | 7,094,995 | 250,811 | - | 245,530 | - | 11,853,651 |
| 2001 | 1,182,130 | 1,296,745 | 1,485 | 162,572 | 100,581 | 249,604 | 4,320,103 | 212,568 | - | 188,981 | - | 7,714,769 |
| 2002 | 1,411,133 | 1,237,060 | 343 | 143,404 | 288,084 | 330,170 | 4,915,809 | 179,481 | - | 184,104 | 8,591 | 8,698,179 |
| 2003 | 903,731 | 623,245 | - | 110,425 | 394,091 | 90,749 | 4,356,619 | 110,022 | - | 90,344 | - | 6,679,226 |
| 2004 | 1,188,360 | 720,181 | - | 129,134 | 281,958 | 105,536 | 7,231,013 | 250,842 | - | 137,300 | - | 10,044,324 |
| 2005 | 985,184 | 593,345 | - | 107,985 | 70,086 | 55,181 | 6,172,133 | 319,539 | - | 74,278 | - | 8,377,731 |
| 2006 | 1,188,230 | 738,482 | - | 133,511 | 48,824 | 113,879 | 8,535,423 | 318,241 | - | 96,668 | - | 11,173,258 |
| 2007 | 891,687 | 460,594 | 1,389 | 162,773 | 26,400 | 75,431 | 8,191,322 | 227,323 | - | 41,518 | - | 10,078,437 |
| 2008 | 989,234 | 476,726 | - | 175,568 | 310,321 | 88,040 | 10,045,071 | 272,583 | - | 195,724 | 60 | 12,553,327 |
| 2009 | 1,026,824 | 212,638 | 224 | 135,301 | 16,554 | 136,936 | 7,544,327 | 436,463 | - | 118,847 | 46 | 9,628,160 |
| 2010 | 713,747 | 350,139 | 212 | 170,130 | 77,161 | 27,522 | 7,907,536 | 316,595 | 270 | 107,808 | 13 | 9,671,133 |
| 2011 | 719,036 | 291,869 | 68 | 151,887 | 327,537 | 41,448 | 8,290,406 | 335,760 | 74 | 43,430 | 30 | 10,201,545 |
| 2012 | 784,061 | 328,582 | 357 | 306,157 | 39,797 | 30,748 | 9,401,446 | 316,340 | 439 | 108,221 | 148 | 11,316,296 |
| 2013 | 736,126 | 372,521 | 185 | 36,166 | 415,399 | 15,689 | 8,701,264 | 445,854 | 1,088 | 48,616 | 395 | 10,773,303 |
| 2014 | 812,357 | 406,436 | 849 | 22,293 | 18,238 | 24,587 | 7,823,982 | 374,357 | 3,611 | 42,453 | 108 | 9,529,271 |
| 2015 | 740,543 | 288,302 | 118 | 217,007 | 6,370 | 15,771 | 7,811,832 | 399,683 | 199 | 33,171 | 32 | 9,513,028 |
| 2016 | 574,826 | 155,254 | 155 | 30,710 | 182,121 | 15,719 | 9,408,329 | 415,516 | 4,251 | 16,842 | 30 | 10,803,753 |
| 2017 | 905,045 | 263,957 | 1,292 | 86,361 | 10,461 | 27,206 | 8,680,022 | 592,256 | 396 | 32,665 | 184 | 10,599,845 |
| 2018 | 565,158 | 191,711 | 521 | 25,757 | 4,067 | 28,767 | 8,041,474 | 535,673 | 1,059 | 51,366 | 103 | 9,445,656 |
| 2019 | 486,525 | 152,386 | 338 | 54,990 | 13,790 | 43,786 | 7,821,260 | 581,941 | 10,378 | 30,893 | 23 | 9,196,310 |
| 2020 | 452,920 | 79,428 | 63 | 33,597 | 25,117 | 8,951 | 7,204,095 | 575,887 | 1,745 | 8,254 | 234 | 8,390,291 |

Note: Other CFCs and HCFCs that are reported in small quantities (e.g., CFC-115 and HCFC-142b) or that are contained in blends with non-ODS (e.g., R-408A) are excluded.

FIG. 11

HFC Refrigerant Reclamation Totals by Year (pounds)

| | HFC-23 | HFC-134a | HFC-227ea | HFC-404A | HFC-407A | HFC-407C | HFC-410A | Other HFCs | Total |
|---|---|---|---|---|---|---|---|---|---|
| 2017 | 1,175 | 1,858,132 | 154,655 | 486,719 | 111,255 | 167,445 | 2,103,404 | 207,481 | 5,090,266 |
| 2018 | 841 | 1,910,240 | 248,178 | 506,639 | 143,254 | 167,248 | 2,043,667 | 230,242 | 5,250,309 |
| 2019 | 642 | 2,399,952 | 1,810 | 485,338 | 105,435 | 213,668 | 2,596,861 | 256,034 | 6,059,740 |
| 2020 | 2,293 | 1,992,632 | 134 | 482,131 | 87,162 | 322,112 | 2,406,556 | 203,603 | 5,496,623 |

Mixed Refrigerant Received Totals by Year (pounds)

| 2010 | 2011 | 2012 | 2013 | 2014 | 2015 | 2016 | 2017 | 2018 | 2019 | 2020 |
|---|---|---|---|---|---|---|---|---|---|---|
| 77,038 | 121,718 | 86,146 | 93,807 | 113,883 | 221,159 | 924,475 | 375,671 | 975,271 | 774,472 | 907,371 |

Note: Mixed refrigerant is material received by reclaimers that contains multiple refrigerants, including ODS and HFCs, potentially in unknown quantities and composition.

These are not blends, which contain specific constituents at specific ratios. Mixed refrigerant totals are included in the Total Refrigerant Received table below.

Total Refrigerant Received Totals by Year (pounds)

| 2010 | 2011 | 2012 | 2013 | 2014 | 2015 | 2016 | 2017 | 2018 | 2019 | 2020 |
|---|---|---|---|---|---|---|---|---|---|---|
| 9,236,800 | 9,128,744 | 10,517,549 | 12,244,890 | 10,240,184 | 11,880,944 | 16,156,981 | 17,373,256 | 18,067,745 | 18,445,030 | 15,811,914 |

Note: Reclaimers were not required to include HFC refrigerants in reports of total amount received until 2017.

FIG. 11A

DROP-IN RECYCLED REFRIGERANT COMPOSITIONS HAVING LOW NET GWP REPLACING R-454B

This application is a divisional of U.S. application Ser. No. 18/172,672, filed Feb. 22, 2023, the entire contents of which are hereby incorporated by reference.

FIELD OF DISCLOSURE

The current disclosure pertains to environmentally friendly recycled refrigerant compositions, that include pentafluoroethane (R-125), difluoromethane (R-32), carbon dioxide ($CO_2$) and trans-1,3,3,3-tetrafluoroprop-1-ene (R-1234ZE), which are ideal as a substitute for a composition of 68.9 wt % difluoromethane and 31.1 wt %2,3,3,3-tetrafluoropropene (R-454B).

BACKGROUND

The need for technologies or applications that address climate change through mitigation or adaptation is crucial. These technologies focus on reducing the amount of carbon in the atmosphere by effectively reusing and repurposing existing high Global Warming Potential (GWP) refrigerants as alternatives to new, virgin refrigerants in both existing and new refrigerant applications.

As the industrial revolution progressed from the 19th century to the 20th century, there was a change from mainly mechanical, steam-powered technologies to technologies that relied on electricity and fossil fuels for energy. The widespread adoption of electricity led to a rapid development in refrigeration technologies that used fluorinated and chlorinated hydrocarbon refrigerants in refrigeration, air conditioning, and heating equipment. However, these refrigerants used during the 20th century were ozone-depleting substances (ODS) with high global warming potential (GWP) and contributed significantly to the global warming crisis. While the burning of fossil fuels certainly released large amounts of carbon dioxide into the atmosphere, refrigerants released into the atmosphere also played a significant role in accelerating the global warming crisis as we entered the 21st century. Therefore, there is an urgent need for innovative technology to control, reduce, and prevent human-caused emissions of greenhouse gases to lower carbon pollution and address the global warming crisis that is affecting our planet today.

Since the 1930s, R-12 ($CCl_2F_2$) and R-22 (1950's—$CHClF_2$) have been used as refrigerants in refrigeration and air conditioning equipment. R-12 is a chlorofluorocarbon (CFC) refrigerant, and R-22 is a hydrochlorofluorocarbon (HCFC) refrigerant. Both CFC and HCFC refrigerants are known to deplete the Earth's ozone layer and contribute to global warming when released into the atmosphere. In 1987, the United States signed the Montreal Protocol on Substances that Deplete the Ozone Layer (Montreal Protocol) to phase out the production and import of R-12 by 1996 and R-22 by 2020. The Clean Air Act's Section 608 also established proper refrigerant management procedures and a ban on venting ozone-depleting refrigerants into the atmosphere in 1993. Section 608 requires service technicians to recover a system's refrigerant and either reuse it in the same system or send it to an EPA certified reclaimer to be destroyed or reclaimed. Since R-12 and R-22 are single-molecule refrigerants, reclaimers commonly use simple fractionation processes to reclaim R-12 and R-22 back to AHRI Standard 700, which is an economical way to recover and reuse these refrigerants instead of venting them into the atmosphere.

The industry responded to the Montreal Protocol by creating refrigerant technology using hydrofluorocarbon (HFC) refrigerants that do not harm the ozone layer. In 1990, HFC refrigerant R-134A was introduced as a substitute for R-12 in vehicles and transportation equipment. A year later, R-410A HFC refrigerant was introduced as a replacement for R-12 and R-22 in residential and light commercial cooling systems. In the early and mid-1990s, work began on HFC refrigerant blends to replace R-12 and R-22 in existing equipment.

R-410A is an HFC refrigerant blend made up of 50 wt % difluoromethane ($CH_2F_2$) R-32 and 50 wt % pentafluoroethane ($CHF_2CF_3$) R-125 and has a global warming potential that is 2,088 times greater than $CO_2$ over a 100-year period. Over the last decade, about 50 million pounds of R-410A were used in new and existing equipment each year. Leaks and venting of R-410A and other CFC, HCFC, and HFC refrigerants continue to contribute to the current global warming crisis. According to the US EPA, reclaimed HFC refrigerants accounted for only 1.6% of all refrigerants sold in the US in 2020.

While HFC based retrofit replacements for R-12 and R-22 gained in popularity, illegal mixing of HFC refrigerant blends with R-22 has resulted in the accumulation of complex refrigerant mixtures that are not listed in the AHRI-700 Standard. The technology to handle these off-spec mixtures has not been developed quickly enough, causing service technicians to pay for the destruction of mixed refrigerants they unknowingly recover. The rise in mixed refrigerants and the decrease in U.S. reclamation rates indicate that more HCFC and HFC refrigerants (ozone-depleting and greenhouse gases) are being released into the atmosphere instead of being recovered and sent to an EPA-approved reclaiming facility.

To comply with the global HFC phase down mandated by the European Union's F-gas Regulations in 2015 and the Kigali Amendment to the Montreal Protocol in 2019, manufacturers of refrigeration equipment worldwide have been working to develop equipment technology that utilizes low-GWP refrigerants. This effort has led to the increasing adoption of low-GWP refrigerants, such as $CO_2$ (R-744), hydrocarbons, hydrofluoroolefins (HFOs), HFC-HFO blends, and the low-GWP HFC R-32. These new refrigerants are used in many commercial refrigeration applications, such as replacing R-404A with $CO_2$, R-290 (propane) as a hydrocarbon replacement for R-134A in small residential and commercial applications, HFO R-1234YF as a replacement for R-134A in automotive air conditioning, HFC-HFO blend R-454B, R-448A, and R-452B in commercial refrigeration applications, and HFC R-32 as a replacement for R-410A (R-32:R-125 (50 wt %:50 wt %)) and R-407C (R-32:R125:R-134A (23 wt %:25 wt %:52 wt %) in small residential split air conditioning systems.

In an effort to reduce the impact that HFC refrigerants have on global warming, the U.S. passed the American Innovation and Manufacturing (AIM) Act in 2020 and ratified the Kigali Amendment to the Montreal Protocol in 2022. The AIM Act gives the U.S. Environmental Protection Agency (EPA) the authority to establish a phasedown schedule for HFC refrigerants and requires the recovery, reclaiming, reusing or destroying of HFC refrigerants in equipment being repaired or taken out of service. Starting in 2022, the phasedown schedule gradually reduces the consumption and production of HFC refrigerants until an 85% reduction in baseline (average annual production and consumption from 2011 to 2013) is achieved by 2036, aligning with the Kigali Amendment to the Montreal Protocol. The EPA uses allowances as a unit of measure to control production and consumption (imports). Each refrigerant is assigned a Metric Tons Exchange Value Equivalent (MTEVe) based on its Global Warming Potential (GWP) compared to $CO_2$, and entities receive their allowance allocation in MTEVe units. This legislation will prevent the equivalent of 900 million tons of carbon dioxide emissions from entering the atmosphere over time, an impact equivalent to preventing the burning of one trillion tons of coal.

In response to the global phasedown of high-GWP refrigerants and the passage of the AIM Act, leading U.S. air conditioning equipment manufacturers have redesigned their residential and light commercial air conditioning equipment to use refrigerants with lower GWP, such as R-454B and R-32. Four out of five of the leading equipment manufacturers in the comfort cooling space will move from R-410A to R-454B-containing equipment in 2023. One manufacturer will build equipment containing R-32. HFCs and HFC-HFO blends like R-32 and R-454B may provide a short-term solution, but it does not address the long-term goal of decarbonization and raises concerns about the life-cycle management of these refrigerants.

R-454B is a mildly flammable (A2L) HFC-HFO blend that is formed from 68.9 wt % difluoromethane $CH_2F_2$ (R-32) and 31.1 wt %2,3,3,3-tetrafluoropropene $CH_2=CFCF_3$ (R-1234yf) with a GWP of 466. R-454B was created as a lower GWP alternative to R-410A and R-32. The performance characteristics of R-454B approximate R-32, but R-454B has a GWP of 466 compared to a GWP OF 675 for R-32 and a GWP of 2,088 for R-410A. It is important to note that R-454B is composed of 31.1 weight percent R-1234yf. However, when R-1234yf is released into the atmosphere, it breaks down into trifluoroacetic acid, which can potentially contaminate the global water supply. R-32 (difluoromethane) is a refrigerant that is already used worldwide and is expected to be one of the preferred transition refrigerants in the U.S. over the next 20 years. R-32 is a mildly flammable (A2L) high-pressure, single-molecule HFC refrigerant with a GWP of 677.

Although R-454B, R-410A, R-32 and R-125 are greenhouse gases, their production and importation will continue to be necessary to charge new equipment that contains R-454B, R-410A, or R-32 and service existing equipment that contains R-410A, or R-32. The AIM Act will reduce HFC production and imports by 70% in 2029, and the market will require a supply of reclaimed R-32 and R-125 to make up for the shortfall in production and imports of R-32, R-125, and R-454B. With nearly 1 billion pounds of HFC refrigerants in the installed equipment base and little enforcement of the prohibition on mixing refrigerants, it is crucial for EPA-certified reclaimers to develop advanced fractionation technology that can refine feed streams of complex refrigerant mixtures, including HCFCs, HFCs, HFOs, hydrocarbons, and flammable components. By filtering and purifying these feed streams back to AHRI Standard 700, specific refrigerant components can be reused in new and existing refrigeration equipment without adding additional global warming pollutants to the atmosphere, thus reducing the need for foreign production of greenhouse gases that contribute to the global warming crisis if released or vented.

Recycling refrigerants, also known as reclamation, is an environmentally friendly solution that allows for the reuse of previously produced refrigerants. This eliminates the need for new production of these materials, which often have a high global warming potential (GWP). By reusing these refrigerants, their GWP is effectively neutralized, as the GWP value is already accounted for at the time of initial production or importation. This means that no further consumption or production allowances are required to reclaim and reuse these materials. Reclaimed refrigerants not only conserve resources but also play a crucial role in reducing carbon emissions and addressing the global warming crisis.

The purpose of the background section in this document is to provide context and understanding of the technology and operations related to the present disclosure. It is intended to assist those with expertise in the field to comprehend the extent and usefulness of the disclosure. Any statements included in this section are not considered prior art unless explicitly stated.

SUMMARY

The following provides a brief overview of the disclosure to assist those familiar with the field in understanding its main concepts. This summary is not meant to be a comprehensive summary of the disclosure or to identify key elements of the disclosed embodiments. Its purpose is to provide a basic understanding of the disclosure before delving into more detailed descriptions later on.

An embodiment of the present disclosure pertains to an environmentally friendly recycled refrigerant composition, which includes R-125 (pentafluoroethane) and R-32 (difluoromethane) with a net zero global warming potential (GWP). This composition can be used as a substitute for R-454B in both new and existing equipment.

An embodiment of the disclosure relates to a refrigerant composition that is a drop-in replacement for R-454B in new and installed equipment. The composition is made up of recycled R-32 and R-125, which have a net global warming potential of 0. It is formed from about 72-74% difluoromethane, about 7-8% pentafluoroethane, about 1-3% $CO_2$ and about 17-19%1,3,3,3-tetrafluoropropene. The composition can be about 72.8% difluoromethane, about 7.2% pentafluoroethane, about 2% $CO_2$ and about 18%1,3,3,3-tetrafluoropropene. These percentages may have a ±2% deviation. The refrigerant composition has a net global warming potential about 29% of that of a mixture of about 68.9 wt % difluoromethane and 31.1 wt % 2,3,3,3-tetrafluoropropene.

In another embodiment, the refrigerant composition has a theoretical boiling point of about −51° F., a liquid phase pressure of about 221 psia at 70° F. and a vapor phase pressure of about 198 psia at 70° F. The refrigerant composition may have a liquid phase density of about 1.02 g/cm³ at 70° F. and a vapor phase density of about 0.043 g/cm³ at 70° F. The refrigerant composition may have a liquid phase enthalpy of about 0.236 KJ/g at 70° F., a vapor phase enthalpy of about 0.480 KJ/g at 70° F., a liquid phase entropy of about $6.2 \times 10^{-4}$ KJ/gR at 70° F., and a vapor phase entropy of about $1.1 \times 10^{-3}$ KJ/gR at 70° F.

In another embodiment, a refrigerant mixture may be about 95-99.99 wt % of a refrigerant composition of the disclosure, and about 0.01-5 wt % lubricant. The lubricant may be mineral oil, alkylbenzene oil or polyol ester. The lubricant may be an ester of at least one neopentyl polyol represented by the structural formula:

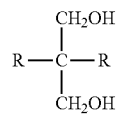

in which each R is independently selected from $CH_3$, $C_2H_5$ or $CH_2OH$.

In another embodiment, the refrigerant mixture may also contain a UV dye or a sealant as an additional component.

In another embodiment, a method for creating a refrigerant composition involves introducing a blend of reclaimed refrigerants, which includes difluoromethane, pentafluoroethane, and chlorodifluoromethane, into the center of a distillation column. The top of the distillation column is used to extract a mixture that is made up of roughly 90-92% difluoromethane and 8-10% pentafluoroethane, while chlorodifluoromethane is removed from the bottom of the column. The refrigerant mixture is made entirely from recycled materials and has a net global warming potential of 0, and the refrigerant mixture is utilized to manufacture the refrigerant composition of the disclosure. The refrigerant mixture contains approximately 91% difluoromethane and 9% pentafluoroethane and contains less than $1.0 \times 10^{-18}$ wt % of water.

BRIEF DESCRIPTION OF THE DRAWINGS

In this disclosure, various embodiments of the present invention will be described using drawings. These drawings are provided to aid in the understanding of the invention and should not be interpreted as limiting the scope of the invention. The embodiments depicted in the drawings are intended to be thorough and complete and convey the full scope of the invention to those skilled in the art. Similar elements in the drawings are identified by like numbers.

FIG. 11 shows the ODS refrigerant reclamation totals by year;

FIG. 11A shows HCF refrigerant reclamation totals by year, mixed refrigerant received totals by year and total refrigerant received totals by year;

DETAILED DESCRIPTION

Figure 1:
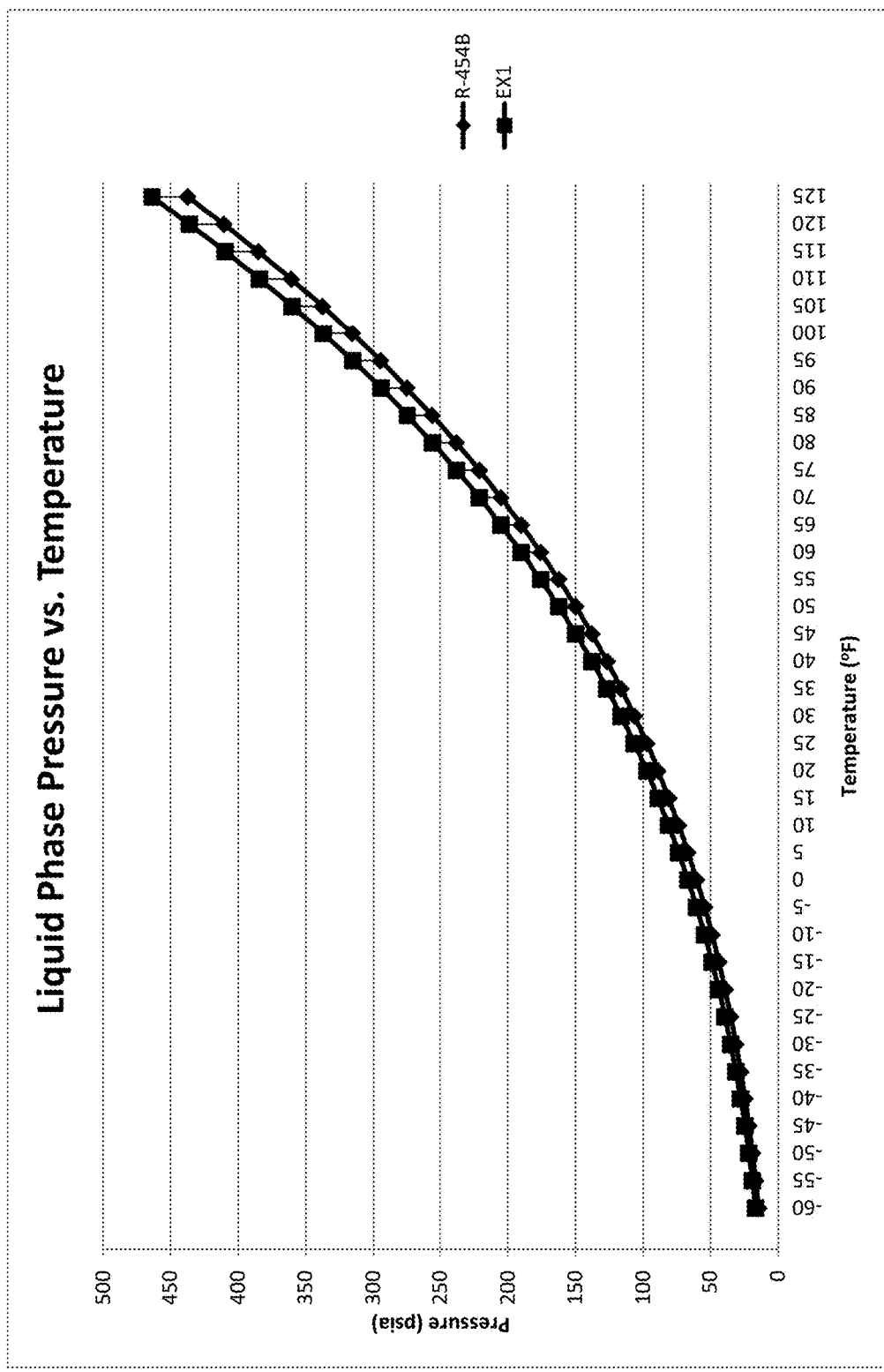
FIG. 1 depicts the liquid phase pressure-temperature curve of the refrigerant compositions of the disclosure compared to R-454B.

For simplicity and illustrative purposes, the present disclosure is described by referring mainly to exemplary embodiments thereof. In the following description, numerous specific details are set forth in order to provide a thorough understanding of the present disclosure. However, it will be readily apparent to one of ordinary skill in the art that the present disclosure may be practiced without limitation to these specific details.

R-32 (difluoromethane) is a newer refrigerant that is already widely used worldwide and is expected to be a preferred transition refrigerant in the U.S. over the next 20 years. Along with R-32, Honeywell/Chemours has also introduced refrigerant R-454B, which is a blend of 68.9% R-32 and 31.1%2,3,3,3-tetrafluoropropene (R-1234YF). However, it is important to note that R-1234YF, when released into the atmosphere, breaks down into trifluoroacetic acid and can ultimately contaminate the water supply globally.

R-454B was created as a lower Global Warming Potential (GWP) alternative to R-410A, which was introduced in 1991 as a replacement for R-12 and R-22 in residential and light commercial comfort cooling equipment. In the early and mid-1990s, work began on developing HFC refrigerant blends as retrofit replacements for most R-12 and R-22 equipment applications.

R-410A is a blend of HFC refrigerants composed of 50% difluoromethane ($CH_2F_2$, R-32) and 50% pentafluoroethane ($CHF_2CF_3$, R-125), with a global warming potential 2,088 times greater than $CO_2$ over a 100-year period. In the last decade, an estimated 50 million pounds of R-410A were used annually in new and existing equipment. However, leaks and venting of R-410A and other CFC, HCFC, and HFC refrigerants continue to contribute to the ongoing global warming crisis. The US Environmental Protection Agency (EPA) reports that reclaimed HFC refrigerants made up only 1.6% of all refrigerants sold in the U.S. in 2020.

R-454B is a replacement for R-410A which is, similar to R-32, primarily used in residential cooling applications, affecting a majority of people in the United States. With a Global Warming Potential (GWP) of 466, compared to a GWP of 675 for R-32, four out of five-unit manufacturers will switch to producing R-454B in 2023. Among major manufacturers, only one will standardize with R-32 over R-454B (68.9% R-32, 31.1%2,3,3,3-tetrafluoropropene (R-1234YF). The performance and characteristics of R-454B approximate R-32, with the added advantage of a superior GWP.

As HFC refrigerant blends gained acceptance as replacements for R-22, the illegal mixing of these blends with R-22 has resulted in an accumulation of complex mixtures of HCFC/HFC/HC refrigerants that are not listed in the AHRI-700 Standard. The technology to reclaim these off-spec refrigerant mixtures has been slow to develop, causing service technicians to incur destruction fees for unknowingly recovering highly mixed refrigerants. The increase in mixed refrigerants and the decrease in U.S. reclamation rates suggest that more HCFC and HFC refrigerants (ODS and greenhouse gases) are being released into the atmosphere instead of being recovered and submitted to an EPA-certified reclaimer.

In response to the global HFC phasedown mandated by the European Union's F-gas Regulations in 2015 and the Kigali Amendment to the Montreal Protocol in 2019, refrigeration equipment manufacturers worldwide have begun developing low-GWP refrigerants and equipment technology. They have adopted an increasing number of low-GWP refrigerants for new equipment, such as $CO_2$ (R-744), hydrocarbons, hydrofluoroolefins (HFOs), HFC-HFO blends, and the low-GWP HFC R-32. These new refrigerants are used in many commercial refrigeration applications, such as replacing R-404A with $CO_2$, R-290 (propane) as a hydrocarbon replacement for R-134A in small residential and commercial applications, HFO R-1234YF as a replacement for R-134A in automotive air conditioning, HFC-HFO blend R-454B (and R-448A and R-452B) in commercial refrigeration applications, and HFC R-32 as a replacement for R-410A (R-32:R-125 (50 wt %:50 wt %)) and R-407C (R-32:R125: R-134A (23 wt %:25 wt %:52 wt %) in small residential split air conditioning systems.

In 2020, the U.S. passed the American Innovation and Manufacturing (AIM) Act, which was ratified by the Kigali Amendment in 2022, in order to reduce the impact of HFC refrigerants on global warming. The AIM Act gives the U.S. Environmental Protection Agency (EPA) the authority to establish a phasedown schedule for HFC refrigerants and requires the recovery, reclaiming, reusing or destroying of HFC refrigerants in equipment being repaired or taken out of service. Starting in 2022, the phasedown schedule gradually reduces the consumption and production of HFC refrigerants until an 85% reduction in baseline (average annual production and consumption from 2011 to 2013) is achieved by 2036, aligning with the Kigali Amendment to the Montreal Protocol. The EPA uses allowances as a unit of measure to control production and consumption (imports). Each refrigerant is assigned a Metric Tons Exchange Value Equivalent (MTEVe) based on its Global Warming Potential (GWP) compared to $CO_2$, and entities receive their allowance allocation in MTEVe units. This legislation will prevent the equivalent of 900 million tons of carbon dioxide emissions from entering the atmosphere over time, an impact equivalent to preventing the burning of one trillion tons of coal.

In response to the global phasedown of high-GWP refrigerants and the passage of the AIM Act, leading U.S. air conditioning equipment manufacturers have redesigned their residential and light commercial air conditioning equipment to use refrigerants with lower GWP, such as R-454B and R-32. R-454B is a mildly flammable (A2L) HFC-HFO blend that is formed from 68.9 wt % difluoromethane $CH_2F_2$ (R-32) and 31.1 wt %2,3,3,3-tetrafluoropropene $CH_2=CFCF3$ (R-1234yf) with a GWP of 466. R-32 is also a mildly flammable (A2L) high-pressure, single-molecule HFC refrigerant with a GWP of 677. While the industry-wide adoption of low-GWP HFCs and HFC-HFO blends like R-32 and R-454B may provide a short-term solution, it does not address the long-term goal of decarbonization and raises concerns about the lifecycle management of these refrigerants. Flammability will be discussed in more detail below.

Although R-32 and R-125 are greenhouse gases, their production and imports will continue to be necessary to charge new equipment and service existing equipment that contains R-454B, R-410A, or R-32. The AIM Act will reduce HFC production and imports by 70% in 2029, and the market will require a supply of reclaimed R-32 and R-125 to make up for the shortfall in production and imports of R-454A, R-32, R-125, and R-454B. With nearly 1 billion pounds of HFC refrigerants in the installed equipment base and little enforcement of the prohibition on mixing refrigerants, it is crucial for EPA-certified reclaimers to develop advanced fractionation technology that can refine feed streams of complex refrigerant mixtures, including HCFCs, HFCs, HFOs, hydrocarbons, and flammable components. By filtering and purifying these feed streams back to AHRI Standard 700, specific refrigerant components can be reused in new and existing refrigeration equipment without adding additional global warming pollutants to the atmosphere, thus reducing the need for foreign production of greenhouse gases that contribute to the global warming crisis if released or vented.

Recycling refrigerants, also known as reclamation, is an environmentally friendly solution that allows for the reuse of previously produced refrigerants. This eliminates the need for new production of these materials, which often have a high global warming potential (GWP). By reusing these refrigerants, their GWP is effectively neutralized, as the GWP value is already accounted for at the time of initial production or importation. This means that no further consumption or production allowances are required to reclaim and reuse these materials. Reclaimed refrigerants not only conserve resources but also play a crucial role in reducing carbon emissions and addressing the global warming crisis.

By utilizing fractionation and reclaim technology, a new refrigerant composition can be created that has a lower flammability and can serve as a direct replacement for R-454B in new equipment and as a secondary refrigerant in all R-32 applications. This new refrigerant composition will have a reduced global warming potential by using reclaimed materials and advanced reclamation techniques. Furthermore, the process of creating this product is highly efficient and does not require any additional materials or energy consumption.

A refrigerant mixture distilled from recovered refrigerants is a drop-in replacement for R-454B and has a minimal net GWP. A typical mixture of recovered HFC refrigerants coming back to refrigerant reclamation facilities can be introduced to a distillation process to produce components of an HFC blend that will work as an R-454B substitute with equivalent levels of performance, reduced flammability characteristics, and net-zero GWP for the reclaimed components.

The nomenclature of the materials used in the disclosure is set forth in Table. 1.

TABLE 1

Description of Refrigerant Materials

| Chemical Name | Formula | Designation |
| --- | --- | --- |
| 1,1,1,2-tetrafluoroethane | $CF_3CH_2F$ | R-134A |
| pentafluoroethane | $CF_3CHF_2$ | R-125 |
| difluoromethane | $CHF_3$ | R-32 |
| chlorodifluoromethane | $CF_3Cl$ | R-22 |
| 1,1,1-trifluoroethane | $CF_3CH_3$ | R-143A |
| 2,3,3,3-tetrafluoropropene | $H_2C=CFCF_3$ | R-1234YF |
| 1,3,3,3-tetrafluoropropene | $CF_3CH=CHF$ | R-1234ZE |
| Carbon Dioxide | $CO_2$ | R-744 |
| 44:52:4 R-125:R-143A:R-134A | | R-404A |
| 26:26:21:7:20 R-32:R-125:R-134A:R-1234ZE:1234YF | | R-448A |
| 67:7:26 R-32:R-125:R-1234YF | | R-452B |
| 68.9:31.1 R-32:R-1234YF | | R-454B |

TABLE 1-continued

Description of Refrigerant Materials

| Chemical Name | Formula | Designation |
|---|---|---|
| 50:50 R-32:R-125* | | R-410A |
| Propane | $CH_3CH_2CH_3$ | R-290 |
| Hydrocarbon | $CH_3(CH_2)_nCH_3$ | HC |

*Proportions in wt %.

R-454B contains R-1234YF, which forms TFF ($CF_3COF$) after reacting with water in the atmosphere to ultimately form TFA ($CF_3COOH$). TFA is known to be contaminating world-wide water supplies. In the atmosphere, there are two decomposition pathways that R-1234YF undergoes. The reactions for the pathways are as follows:

$$CH_2=CFCF_3 + OH \rightarrow CF_3COF + HCHO + H_2O + XO_2 \quad (1)$$

$$CH_2=CFCF_3 + Cl^- \rightarrow 0.92\ CF_3COF + 0.568\ HC(O)Cl + 2XO_2 + CO. \quad (2)$$

There are also reactions with ozone ($O_3$) and nitrate radical (—$NO_3$), although these are considered of minor importance. The products (intermediate) of pathway (1) are TFF and formaldehyde (HCHO) and of pathway (2) are TFF and formyl chloride (HC(O)Cl). TFF then reacts rapidly with atmospheric moisture ($H_2$) to form trifluoroacetic acid ($CF_3COOH$, TFA):

$$CF_3COF + H_2O \rightarrow CF_3COOH + CO_2 + HF \quad (3)$$

The dominant degradation pathway of R-1234YF is via reaction with hydroxyl radicals. The first step in the process is the addition of —OH to one or other of the carbon atoms attached to the double bond, this being the rate determining step. This is followed by a series of oxidation reactions involving molecular oxygen and nitric oxide, resulting in the intermediates TFF and HCHO given in pathway (1) above.

The mechanism of the degradation arises from R-1234YF having 4 fluorine atoms on one side of the double bond, where the structure is $CH_2=CFCF_3$. The attack is thus:

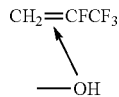

The result is that all 4 fluorine atoms are present in the decomposition product $CF_3COF$ (TFF), representing the decomposition product from the right side of the double bond.

In contrast, for R-1234ZE, one fluorine atom is on the left side of the double bond and three fluorine atoms on the right side of the double bond. The attack is thus:

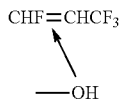

The decomposition products are HCOF and $CF_3COH$, which are the two oxygenated products resulting from the splitting of the molecule at the double bond. Therefore, R-1234ZE does not form TFF.

That is, for R-1234ZE, the thermally unstable intermediates trifluoroacetaldehyde, $CF_3C(O)H$, and formyl fluoride, HC(O)F, do not exist for long in the environment with $CF_3C(O)H$ photolyzed by sunlight in the lower atmosphere, giving it a lifetime of 4 days. It is removed four times as fast as it is formed from R-1234ZE so it cannot accumulate in the atmosphere. Formyl fluoride dissolves in environmental water where it is rapidly hydrolyzed to hydrofluoric acid, HF, and formic acid, HC(O)OH. R-1234ZE is thus the preferred alternative from an environmental standpoint.

The product of the disclosure is a replacement for R-454B primarily in home cooling applications and impacts nearly every person in the United States. The disclosed formulation serves as a direct drop-in for R-454B in new applications as well as make-up gas for the installed equipment base, both of which are classified as A2L. The disclosed formulation is shown in Table 2 below as a direct replacement for R-454B, R-410A, as well as R-32.

TABLE 2

Formulations of the Disclosure Compared to R-454B, R-410A and R-32.

| Product | EX1 | R-454B | R-410A | R-32 |
|---|---|---|---|---|
| R-125 | 7.2 wt % | 0.0 wt % | 50.00 wt % | 0.00 wt % |
| R-32 | 72.8 wt % | 68.9 wt % | 50.00 wt % | 100.0 wt % |
| $CO_2$ | 2.0 wt % | 0.0 wt % | | |
| R-1234ZE | 18.0 wt % | 0.0 wt % | | |
| R-1234YF | 0.0 wt % | 31.1 wt % | | |
| Total | 100.0 wt % | 100.0 wt % | 100.0 wt % | 100.0 wt % |
| Pressure at 70° F. (psia) | 221 | 205 | 216 | 221 |
| GWP | 744 | 466 | 2087 | 675 |
| 100% Reclaim GWP | 0 | — | — | — |
| 80% Reclaim GWP | 149 | — | — | — |
| Theoretical BP (° F.) | −51.3 | – | −58.0 | −61.6 |

*These formulas have a variation of up to ±2%. The values were generated using the NIST REFPROP program.

The refrigerant mixture disclosed in this embodiment is formulated using a 100% reclaimed mixture of R-32 and R-125, with a proportion of 91:9 wt %. This corresponds to the 72.8:7.2 R-32:R-125 ratio used in EX1, which is a drop-in replacement for R-454B. This allows for a significant reduction in GWP, as GWP is only assigned during the production of virgin chemicals, and not for recycled materials. This results in a net GWP of 149 for EX1. Additionally, the inclusion of 2% $CO_2$, which has a GWP of 1, further lowers the overall GWP of the mixture to 134. This represents a significant reduction compared to the GWP of R-454B, which is 29% of its GWP, and 20% of R-32. Additionally, using recycled R-1234ZE can further lower the net GWP.

The main goal of the disclosed refrigerant mixture is to create a product that can be used as a direct replacement for R-454B, while also utilizing reclaimed refrigerant for the R-32 and R-125 components. This not only reduces its global warming potential, but also makes it less flammable than R-454B. Additionally, this refrigerant can also be used as a drop-in replacement for R-32 in various applications.

FIG. 1 shows the liquid pressure (psia) versus temperature relationship of the EX1 product of the disclosure compared to R-454B. As can be seen, there is a close correlation with the R-454B, especially at the lower part of the temperature range, where the curves overlap.

Figure 2:
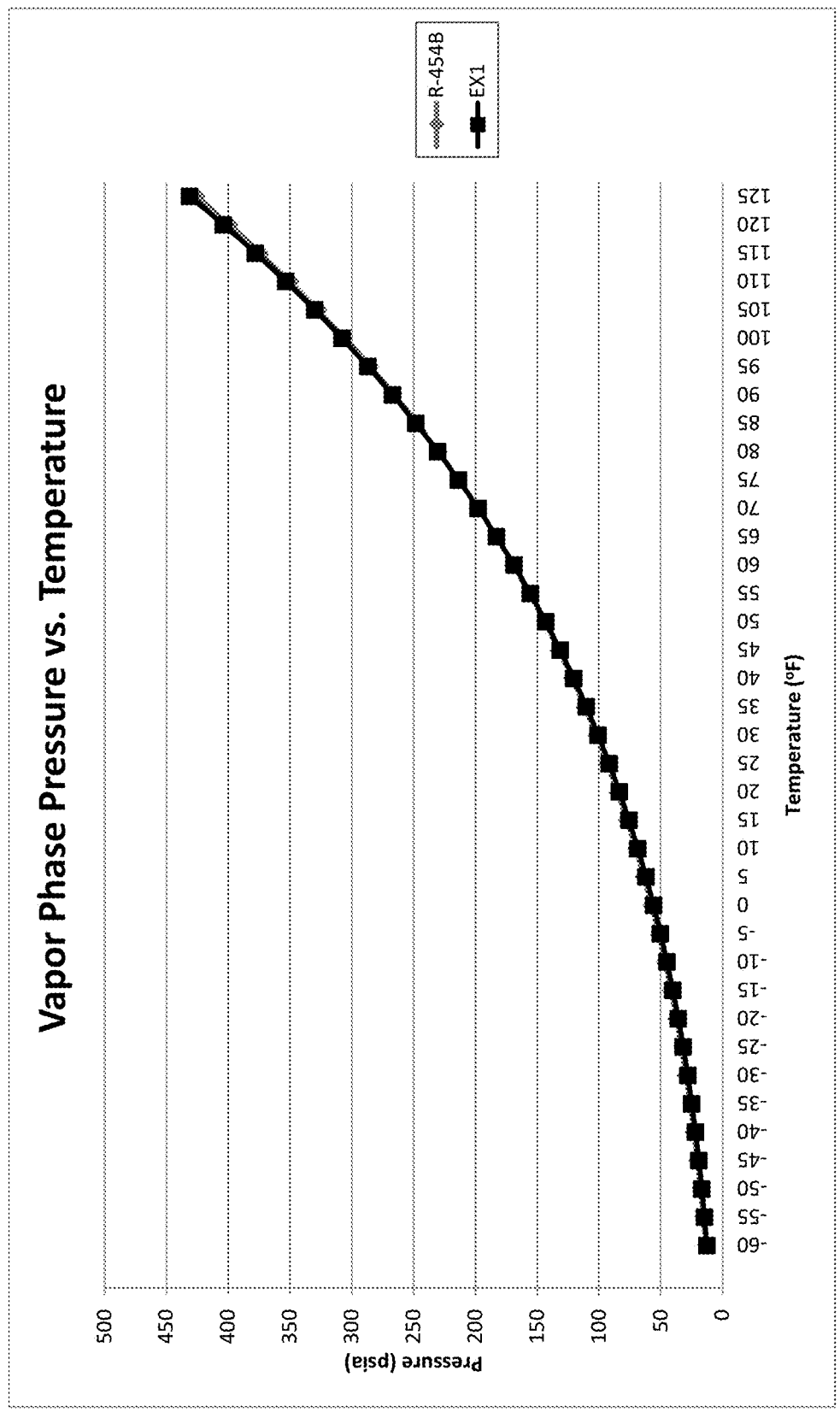
FIG. 2 depicts the vapor-phase pressure-temperature curve of the refrigerant compositions of the disclosure compared to R-454B.

FIG. 2 shows the vapor phase pressure (psia) versus temperature (° F.) relationship of the EX1 product of the disclosure compared to R-454B. As can be seen there is almost complete overlap over the entire temperature range from −60° F. to 125° F.

Figure 3:
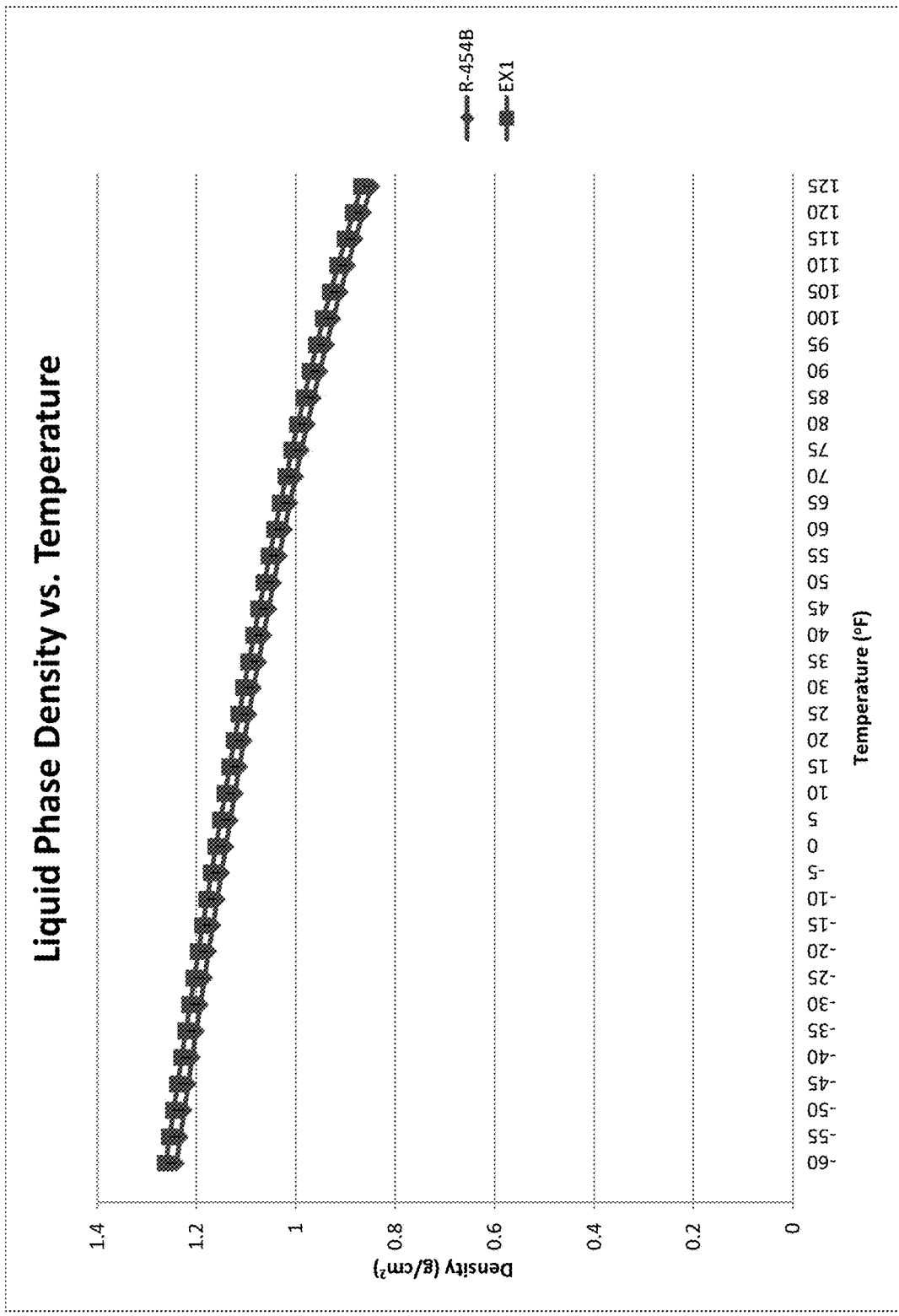
FIG. 3 depicts the liquid density-temperature curve of the refrigerant compositions of the disclosure compared to R-454B.

FIG. 3 shows the liquid phase density ($g/cm^3$) versus temperature (OF) of the EX1 product of the disclosure compared to R-454B. There is a close correlation throughout the temperature range, with R-454B having a slightly lower density.

Figure 4:
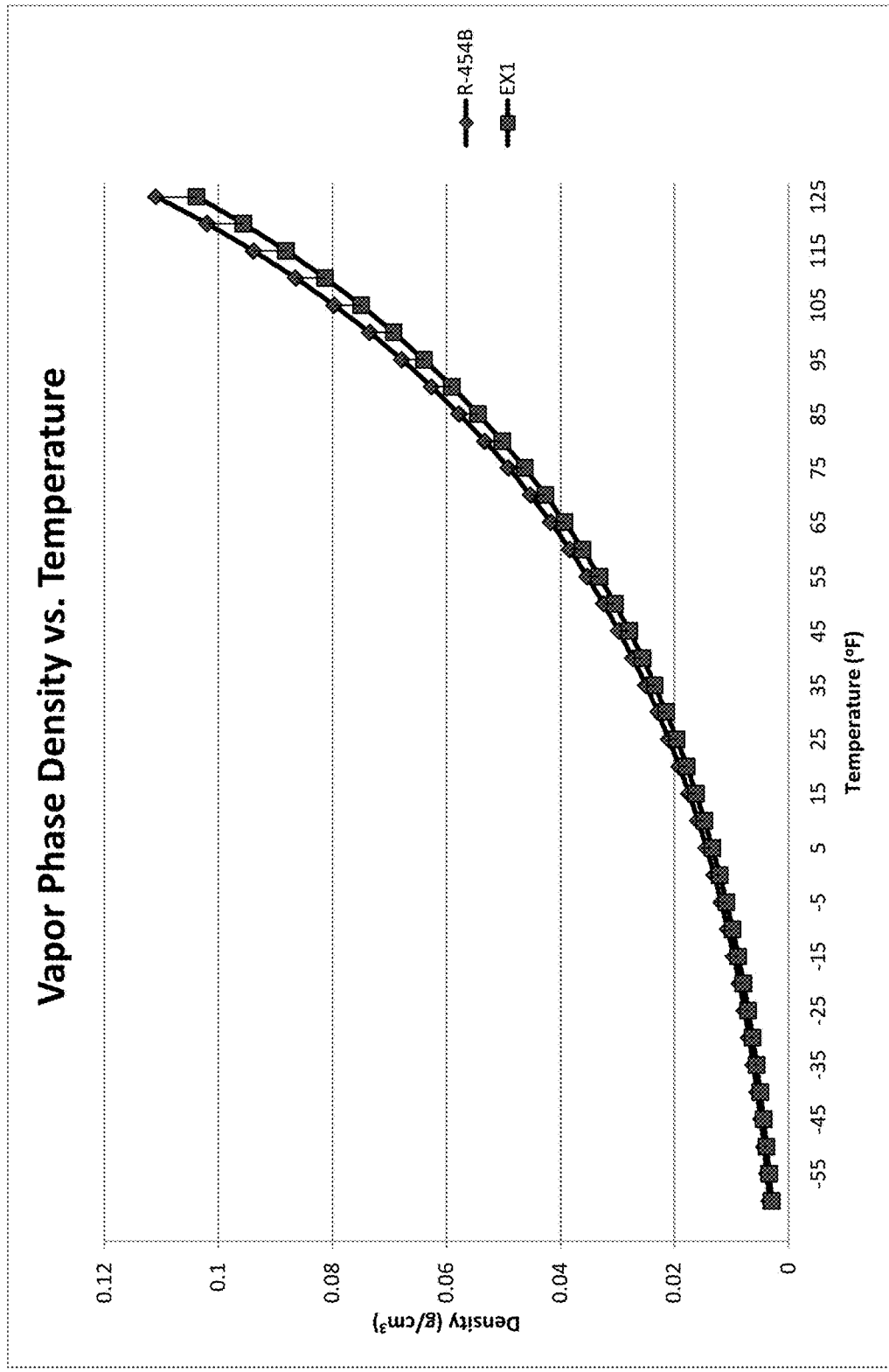
FIG. 4 depicts the vapor density-temperature curve of the refrigerant compositions of the disclosure compared to R-454B.

FIG. 4 shows the vapor phase density ($g/cm^3$) versus temperature (° F.) of the EX1 product of the disclosure compared to R-454B. There is close correlation at lower temperatures, especially those corresponding to refrigeration. At higher temperatures there is more variance with the EX1 mixture still closely tracking the performance of R-454B.

Figure 5:
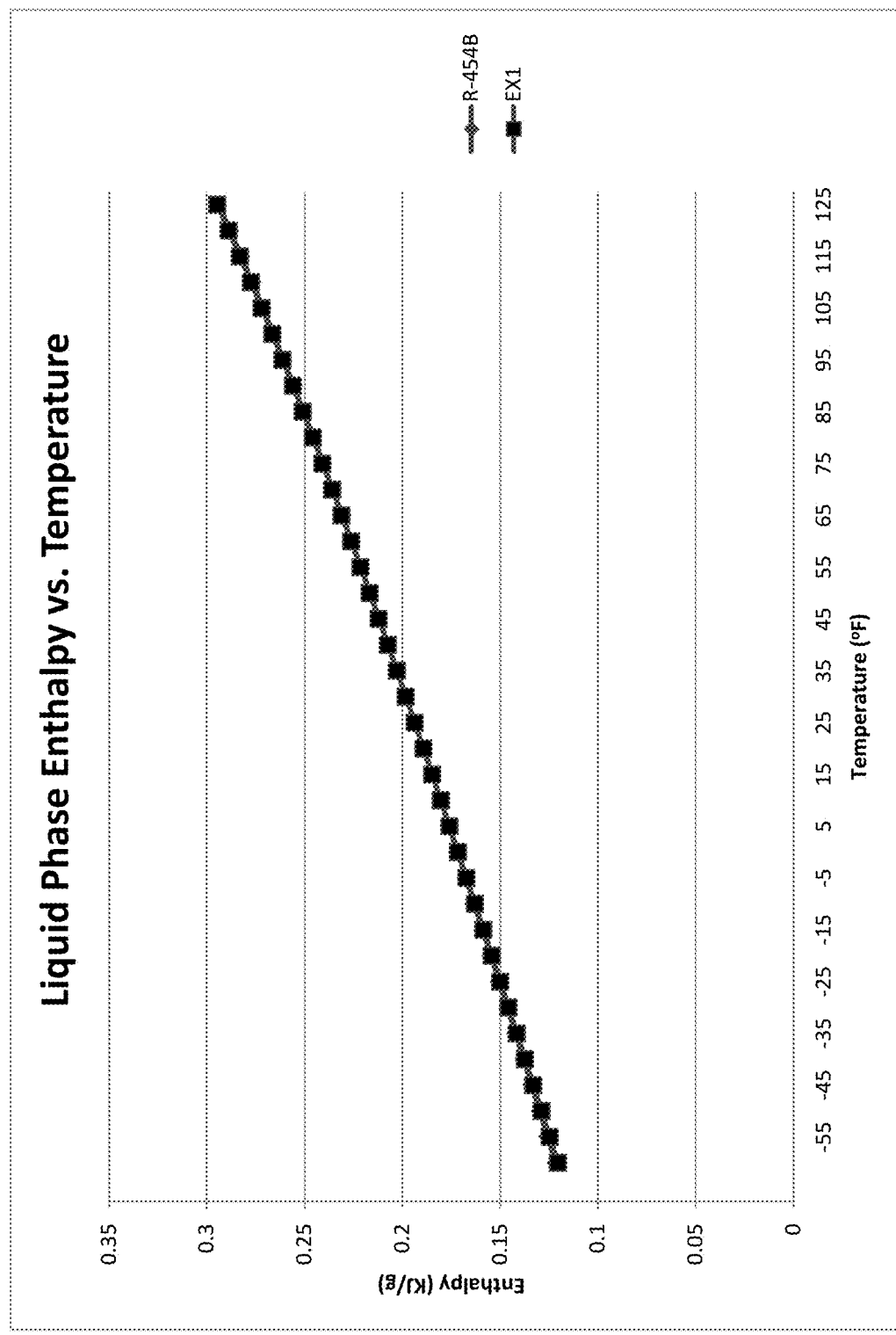
FIG. 5 depicts the liquid phase enthalpy versus temperature curve of the refrigerant compositions of the disclosure compared to R-454B.

FIG. 5 shows the liquid phase enthalpy (KJ/g) versus temperature (° F.) relationship of the EX1 product of the disclosure compared to R-454B. As can be seen, there is a close correlation over the entire temperature range.

Figure 6:
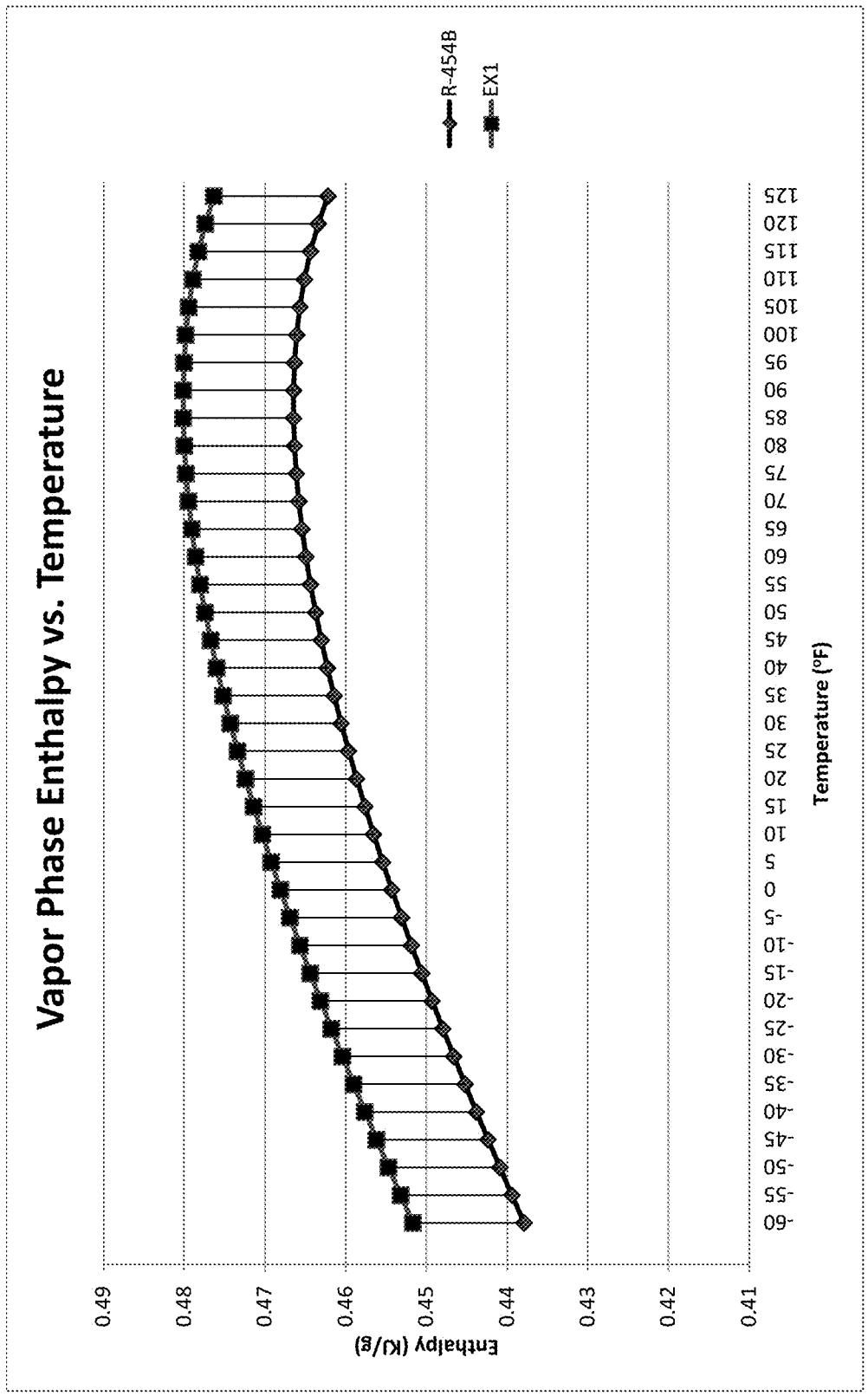
FIG. 6 depicts the vapor phase enthalpy versus temperature curve of the refrigerant compositions of the disclosure compared to R-454B.

FIG. 6 shows the vapor phase enthalpy (KJ/g) versus temperature (° F.) relationship of the EX1 product of the disclosure compared to R-454B. As can be seen, there is a close correlation over the temperature range.

Figure 7:
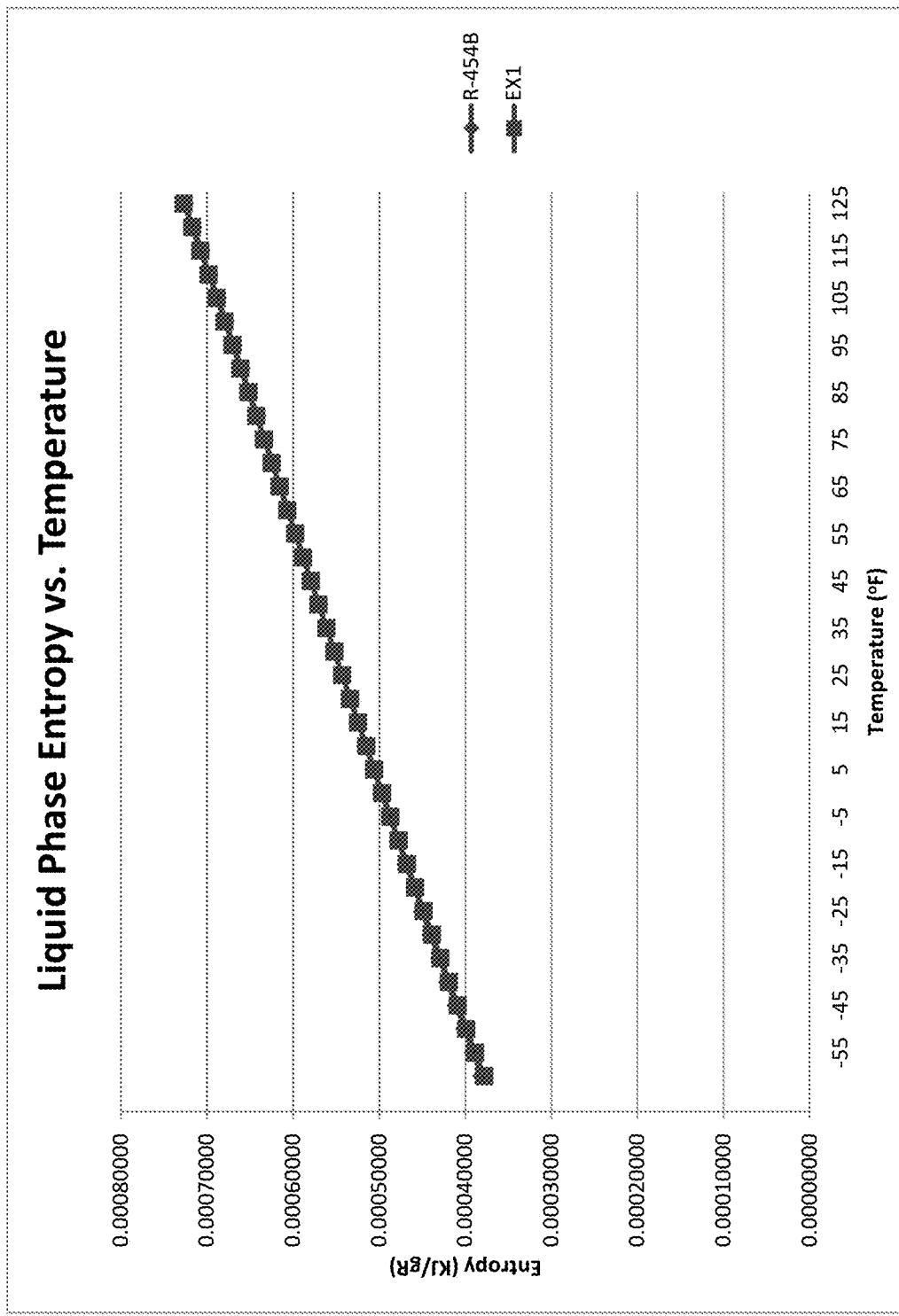
FIG. 7 depicts the liquid phase entropy versus temperature curve of the refrigerant compositions of the disclosure compared to R-454B.

FIG. 7 shows the liquid phase entropy (KJ/gR) versus temperature (° F.) relationship of the EX1 product of the disclosure compared to R-454B. As can be seen, there is a close correlation over the entire temperature range with a very tight overlap.

Figure 8:
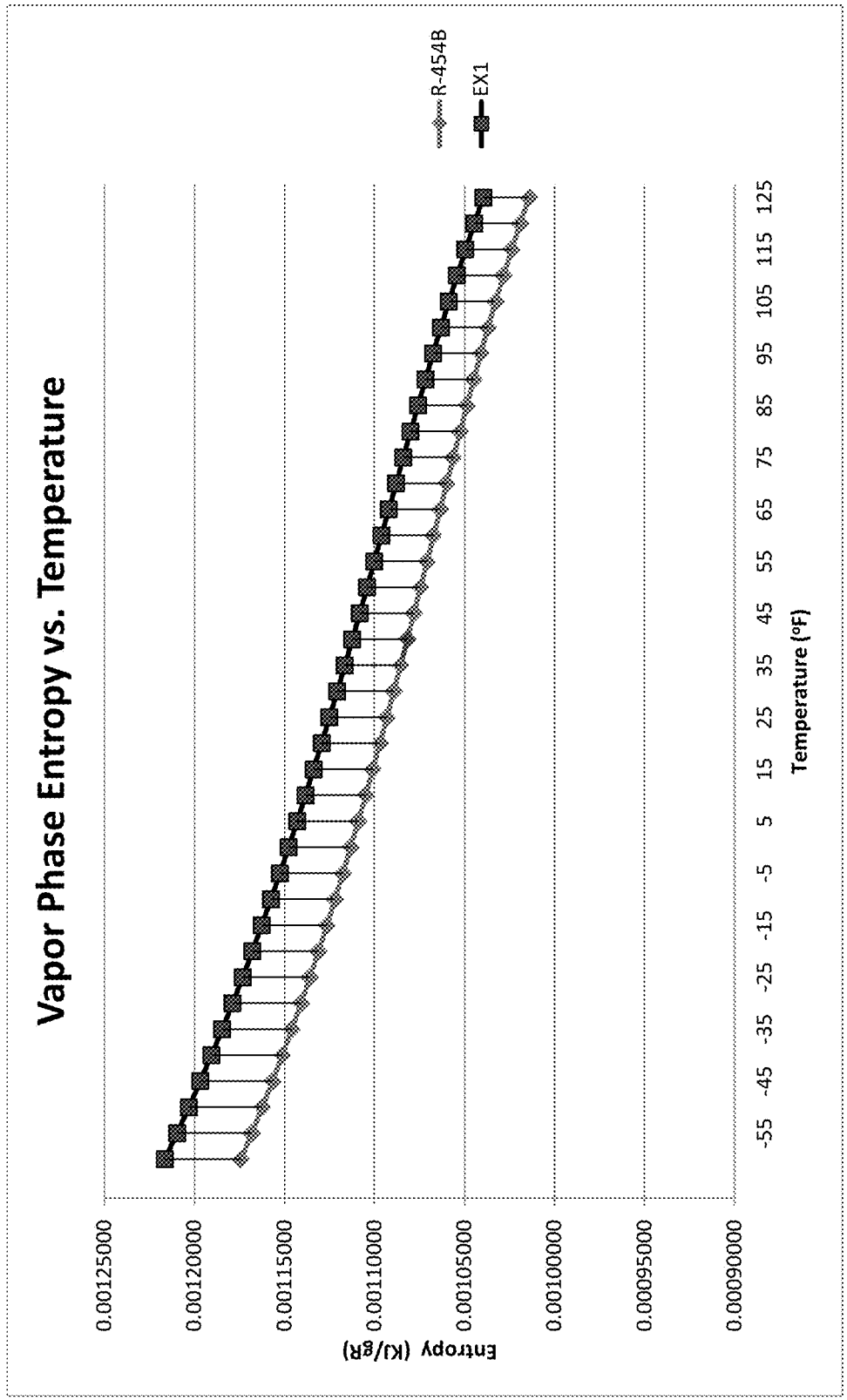
FIG. 8 depicts the vapor phase entropy versus temperature curve of the refrigerant compositions of the disclosure compared to R-454B.

FIG. 8 shows the vapor phase entropy (KJ/gR) versus temperature (F) relationship of the EX1 product of the disclosure compared to R-454B. As can be seen, there is a close correlation with EX1 having a slightly higher entropy, but there is no appreciable effect on heat transfer efficiency.

The thermodynamic properties of the refrigerant mixtures of the disclosure at 70° F. compared to R-454B, R-410A and R-32 are shown in Table 3.

TABLE 3

Thermodynamic Properties of the Refrigerant Mixture of the Disclosure Compared to R-454B, R-410A and R-32 at 70° F.

| Material | Liquid Phase Pressure (psia) | Vapor Phase Pressure (psia) | Liquid Phase Density ($g/cm^3$) | Vapor Phase Density ($g/cm^3$) | Liquid Phase Enthalpy (kJ/g) | Vapor Phase Enthalpy (kJ/g) | Liquid Phase Entropy (kJ/gR) | Vapor Phase Entropy (kJ/gR) |
|---|---|---|---|---|---|---|---|---|
| EX1 | 221 | 198 | 1.02 | 0.043 | 0.236 | 0.480 | $6.2 \times 10^{-4}$ | $1.1 \times 10^{-3}$ |
| R-32:125-91:9* | 221 | 221 | 0.995 | 0.045 | 0.237 | 0.498 | $6.3 \times 10^{-4}$ | $1.1 \times 10^{-3}$ |
| R-454B | 205 | 198 | 1.00 | 0.045 | 0.235 | 0.466 | $6.2 \times 10^{-4}$ | $1.1 \times 10^{-3}$ |
| R-32 | 221 | 221 | 0.977 | 0.042 | 0.238 | 0.517 | $6.3 \times 10^{-4}$ | $1.2 \times 10^{-3}$ |
| R-410A | 216 | 216 | 1.078 | 0.059 | 0.233 | 0.426 | $6.2 \times 10^{-4}$ | $1.0 \times 10^{-3}$ |

*Recycled material with net 0 GWP utilized in the manufacture of EX1.

As can be seen, the EX1 has properties approximating those of R-454B and is thus an excellent drop-in replacement for R-454B. EX1 can also be used as a drop-in replacement for R-32.

The data in Table 3 can be compared to the properties at 0° F. shown in Table 4:

TABLE 4

Thermodynamic Properties of Refrigerant Mixtures of the Disclosure Compared to R-454B, R-410A and R-32 at 0° F.

| Material | Liquid Phase Pressure (psia) | Vapor Phase Pressure (psia) | Liquid Phase Density ($g/cm^3$) | Vapor Phase Density ($g/cm^3$) | Liquid Phase Enthalpy (kJ/g) | Vapor Phase Enthalpy (kJ/g) | Liquid Phase Entropy (kJ/gR) | Vapor Phase Entropy (kJ/gR) |
|---|---|---|---|---|---|---|---|---|
| EX1 | 66.5 | 55.8 | 1.16 | 0.012 | 0.17 | 0.47 | $5.0 \times 10^{-4}$ | $1.1 \times 10^{-3}$ |
| R-32:125-91:9* | 64.1 | 64.1 | 1.14 | 0.013 | 0.17 | 0.49 | $4.9 \times 10^{-4}$ | $1.2 \times 10^{-3}$ |
| R-454B | 60.0 | 57.4 | 1.14 | 0.013 | 0.17 | 0.45 | $5.0 \times 10^{-4}$ | $1.1 \times 10^{-3}$ |

TABLE 4-continued

Thermodynamic Properties of Refrigerant Mixtures of the
Disclosure Compared to R-454B, R-410A and R-32 at 0° F.

| Material | Liquid Phase Pressure (psia) | Vapor Phase Pressure (psia) | Liquid Phase Density (g/cm$^3$) | Vapor Phase Density (g/cm$^3$) | Liquid Phase Enthalpy (kJ/g) | Vapor Phase Enthalpy (kJ/g) | Liquid Phase Entropy (kJ/gR) | Vapor Phase Entropy (kJ/gR) |
|---|---|---|---|---|---|---|---|---|
| R-32 | 64.0 | 64.0 | 1.11 | 0.012 | 0.17 | 0.51 | $4.9 \times 10^{-4}$ | $1.2 \times 10^{-3}$ |
| R-410A | 63.1 | 63.0 | 1.24 | 0.017 | 0.17 | 0.41 | $5.0 \times 10^{-4}$ | $1.0 \times 10^{-3}$ |

*Recycled material with net 0 GWP utilized in the manufacture of EX1.

Here again, the EX1 has properties similar to or matching R-454B and is thus an excellent drop-in replacement for R-454B. EX1 can also be used as a drop-in replacement for R-32. Tables 3 and 4 show that the entropies for R454B and EX1 are the same, indicating that the two formulations have the same refrigeration efficiencies.

The R-32:R-125 91:9 mixture is advantageous because it can be incorporated into the EX1 formulation and can be obtained directly from a one-pass distillation of reclaimed refrigerants to yield a product having 0 net GWP, which can be used in the manufacture of the EX1 replacement for R-454B to yield a low GWP drop-in. This R-32:R-125 91:9 mixture also has unexpectedly superior thermodynamic efficiencies as can be seen in FIGS. 9 and 10.

Figure 9:
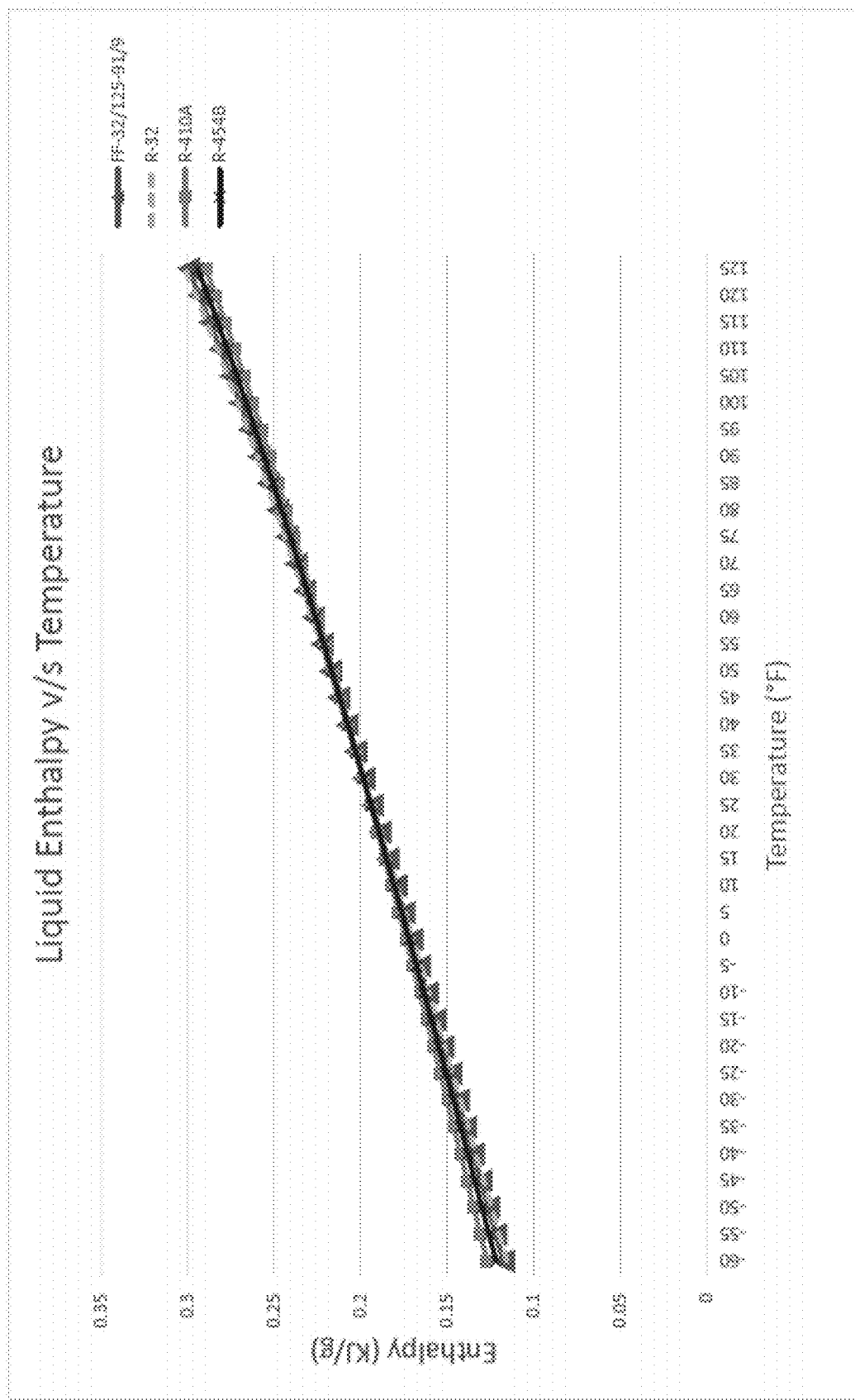
FIG. 9 depicts the liquid phase enthalpy of a 0 net GWP refrigerant composition of the disclosure compared to R-454B and other refrigerants.

FIG. 9 is a graph showing the liquid phase enthalpy of the R-32:R-125 91:9 refrigerant mixture of the disclosure compared to R-454B and other refrigerants. The R-32/125 91:9 mixture, which can be obtained with net 0 GWP, very closely tracks the performance of R-454B throughout the temperature range.

Figure 10:
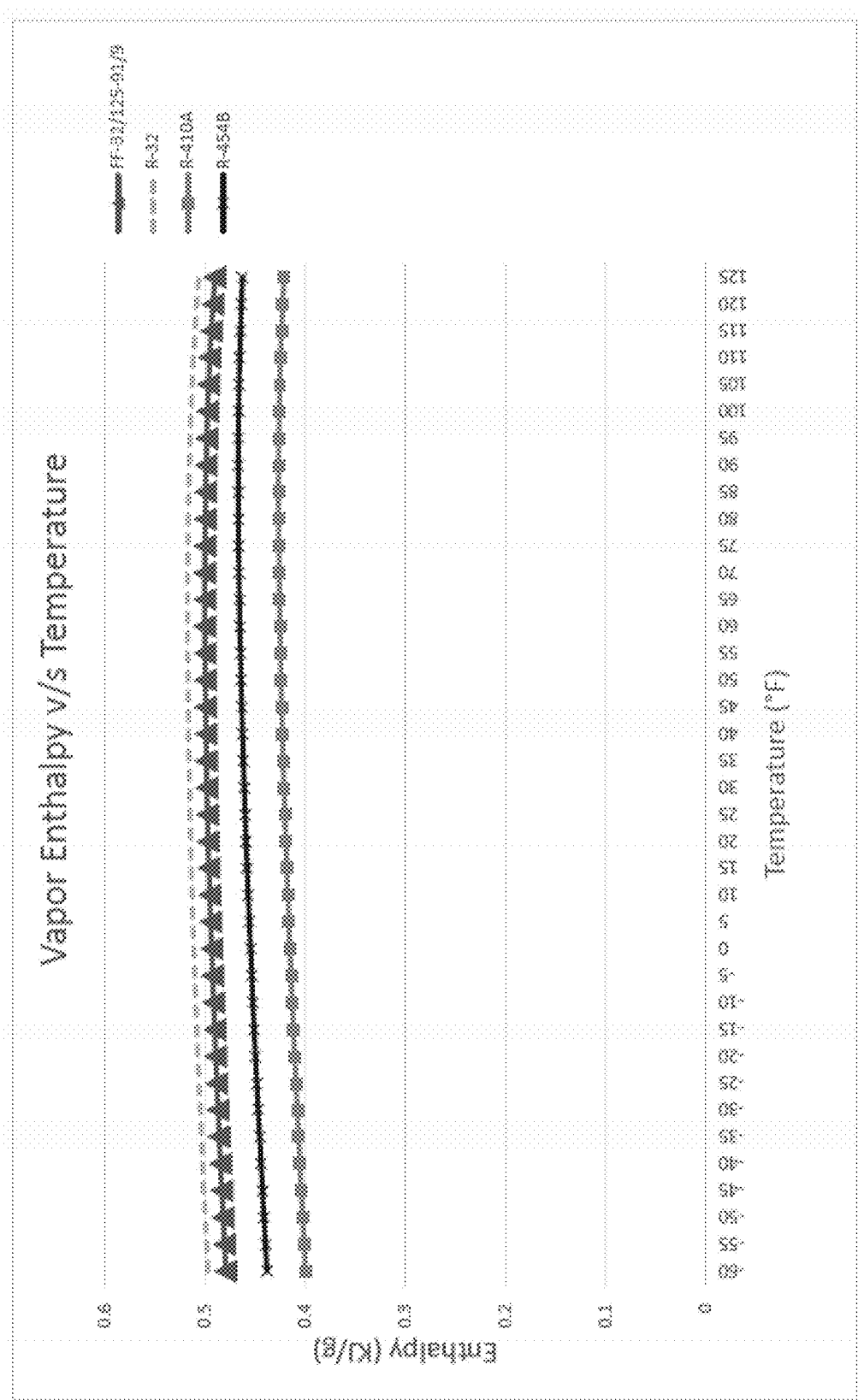
FIG. 10 depicts the vapor phase enthalpy of a 0 net GWP refrigerant composition of the disclosure compared to R-454B and other refrigerants.

This performance is echoed in the graph of vapor phase enthalpy versus temperature shown in FIG. 10. Similarly, R-32:R-125 91:9 refrigerant mixture performs very close to R-454B. Although the vapor phase enthalpy is slightly higher that of R-454B, the results in FIGS. 9 and 10 indicated that the R-32:R-125 91:9 refrigerant mixture is suitable as the basis of a formulation usable as a drop-in replacement for R-454B. Accordingly, the R-32:R-125 91:9 refrigerant mixture will result in a formulation with a drastically reduced GWP of about 20% or even about 18% (when factoring in the $CO_2$ content) of all virgin EX1, or about 32% and 29% of the 466 GWP of R-454B.

Reclamation Streams and Background

FIG. 11 and FIG. 11A shows a summary of data from the U.S. EPA on the reclamation history of ozone-depleting substances (ODS) and hydrofluorocarbons (HFCs). It is evident that there is a growing category of "mixed" HFCs, which includes R-454B. These highly mixed HFCs, which can also contain ODS streams, are becoming a significant source of carbon pollution with no known uses. Conventional HFC/HFO blends, even if they have lower global warming potential (GWP), will continue to contribute to this mixed category or will be released into the atmosphere at the end of their life without appropriate technology for recycling and decarbonization. In contrast, the formulations of the disclosure have zero net GWP or low net GWP and thus eliminate the environmental burden caused by virgin formulations.

Figure 12:
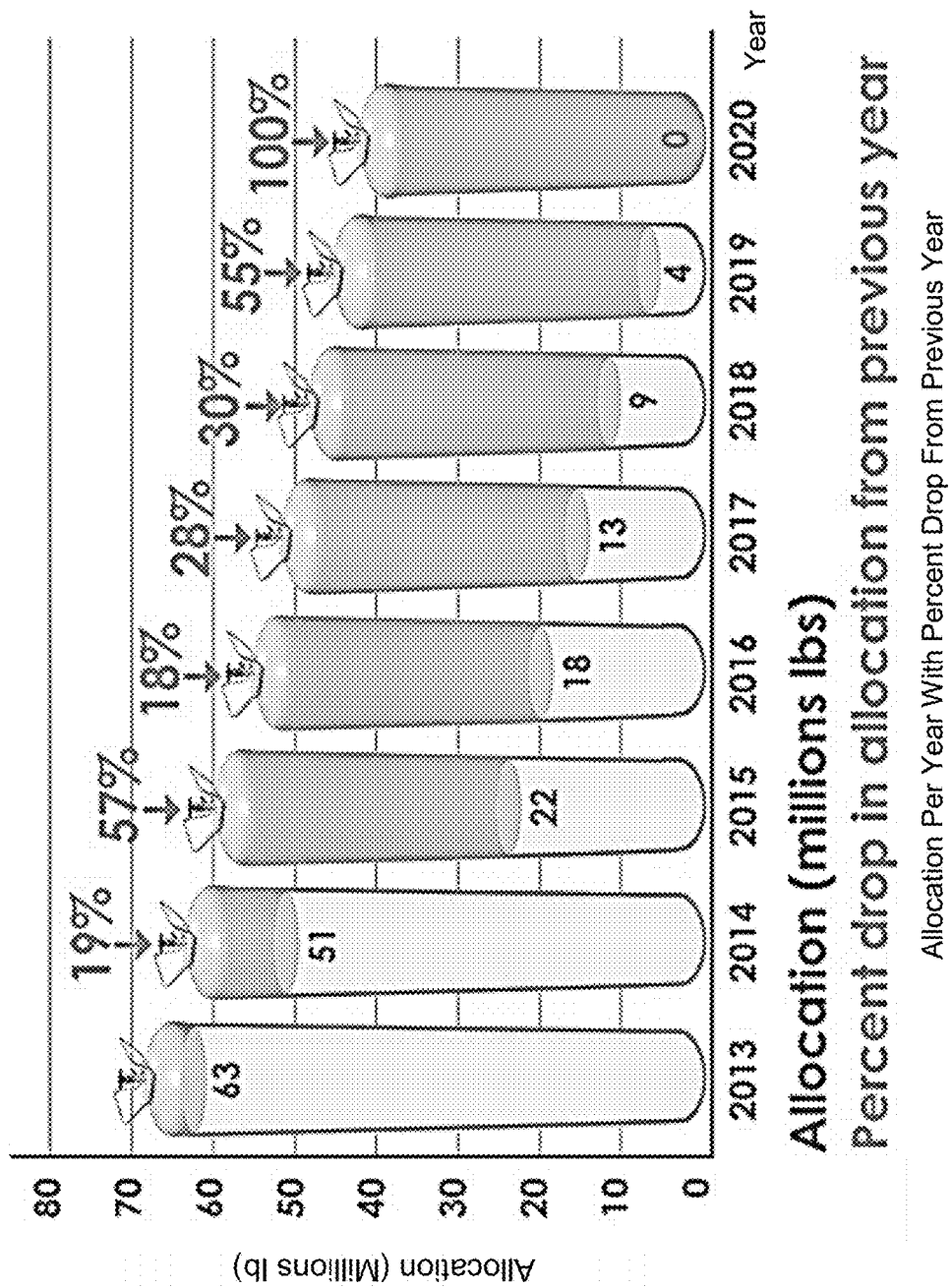
FIG. 12 depicts the R-22 phase-out schedule.

Although the phase-out schedule for Ozone-Depleting Substances (ODS) such as R-22 is illustrated in FIG. 12, with a zero-pound allocation for 2020, R-22 remains the most widely reclaimed product in the United States. Based on historical trends, it will take several years for R-22 to be phased out completely. R-22, being a single molecule, is much simpler to reclaim through single plate distillation than complex HFC blends and mixed HFCs, which require advanced technology for reprocessing.

Figure 13:
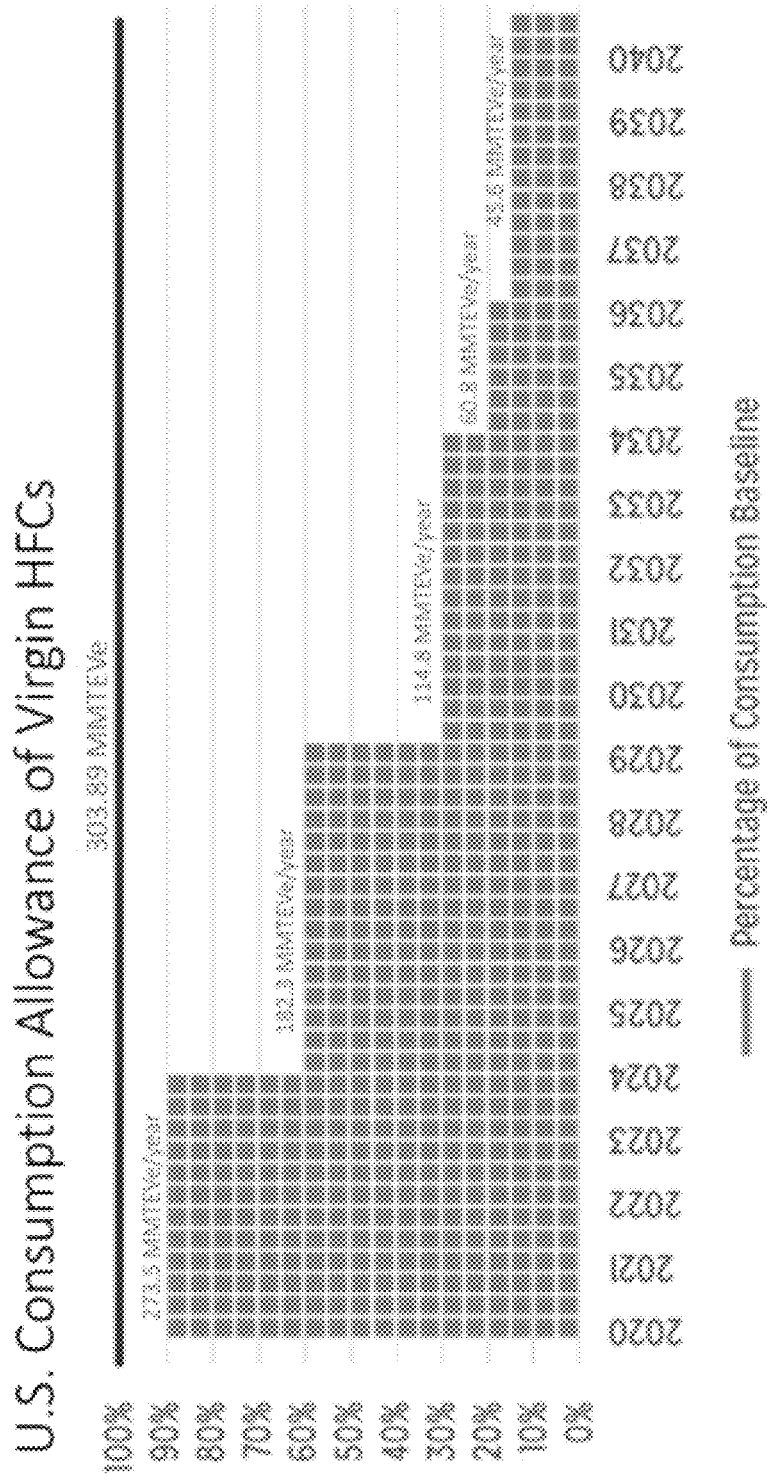
FIG. 13 depicts the U.S. consumption allowance of virgin HFCs.

The graph in FIG. 13 illustrates the decreasing consumption of virgin HFCs in the United States over a 20-year period, from 2022 to 2040. The allowance starts at 273.5 metric tons per year in the beginning and gradually decreases to 45.6 metric tons per year by the end, representing a 15% reduction compared to the 303.89 metric tons per year baseline.

Figure 14:
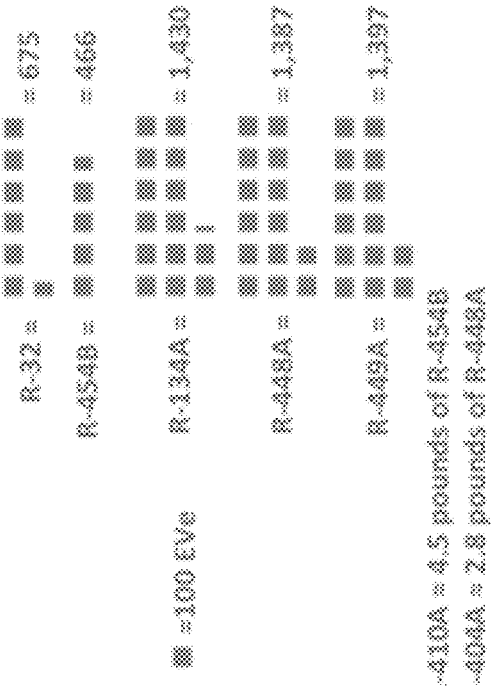
FIG. 14 depicts low-GWP alternatives for HFC phase-down.

FIG. 14 illustrates the comparison of low GWP alternatives to traditional refrigerants, such as R-454B, R-410A, R-404A, and R-448A. It demonstrates that one pound of R-410A is equivalent to 4.5 pounds of R-454B and one pound of R-404A is equivalent to 2.8 pounds of R-448A. The low GWP of the refrigerant composition of the disclosure, EX1, makes it a highly favorable alternative to R-454B.

The refrigerant formulation of the disclosure is made up of reclaimed materials that have been reprocessed to meet the purity standards set by the Environmental Protection Agency (EPA) in accordance with 40 C.F.R. § 82, subpart F. These standards are based on the American Society of Heating, Refrigerating and Air-Conditioning Engineers (ASHRAE) Standard 700-1993 and involve using specific analytical methodology to ensure the purity of the reclaimed refrigerant. The EPA also mandates that refrigerant can only be considered reclaimed if it is recovered by a certified technician, placed in a specific type of container, and not intended to be used in the same system from which it was initially recovered.

In the disclosure, the refrigerant must be reclaimed to the AHRI Standard 700 purity level by a certified reclaimer. This ensures that the used refrigerant is of high quality and will not cause damage to air-conditioning and refrigeration equipment. The use of contaminated refrigerants can lead to increased repair costs, shortened maintenance intervals, decreased equipment lifespan, increased leak rates, and a loss of consumer confidence in reclaimed refrigerants. Once the reclaimed refrigerant meets the standard, it can be used in the formulations of the disclosure, either partially or entirely.

The use of reclaimed materials in the refrigerant formulations of the disclosure results in a significant decrease in global warming potential (GWP), as the reclaimed material is not emitted into the atmosphere. Formulations that utilize entirely reclaimed material have a net GWP of approximately 0, reducing the need for the operation of virgin HFC/HFO facilities around the world.

Flammability

Another issue for refrigerants is flammability. The most well-established classification for this is the ASHRAE classification. There are 3 classifications of flammability in AHRI. Category A1 is "non-flammable," category A2 is "mildly flammable," and category A3 is "flammable." R-32 falls under the "mildly" flammable category while R-410A, for example, is classified as "non-flammable" (A1). Using the disclosed formulation will not require additional flammability considerations as it is a direct replacement for R-454B in new applications and can be used as makeup gas at lower flammability considerations as an A2L. Among major manufacturers, only one will standardize with R-32 over R-454B (68.9% R-32, 31.1%2,3,3,3-tetrafluoropropene (R-1234YF). The performance and characteristics of R-454B approximate or match those of R-32, with the added advantage of a superior GWP.

R-454B is a mildly flammable (A2L) HFC-HFO blend that contains of 68.9 wt % difluoromethane $CH_2F_2$ (R-32) and 31.1 wt %2,3,3,3-tetrafluoropropene $CH_2=CFCF3$ (R-1234yf) with a GWP of 466. R-32 is also a mildly flammable (A2L) high-pressure, single-molecule HFC refrigerant with a GWP of 677, R-410A (combination of R-32 and R-125), for example, receives an A1 "non-flammable" category. In comparison, R-32 receives a "mildly flammable" designation. The disclosed formulation serves as a direct drop-in for R-454B in new applications as well as make-up gas for the installed equipment base, both of which are classified as A1.

Refrigerants such as R-410A, R-407A and R-404A are Class 1 (A1) in their flammability, so do not show flame propagation when tested at 100° C. and 101.3 kPa in air. Class 2 (A2) refrigerants are those with flammability lower than 0.10 kg/m3 at 100° C. and 101.3 kPa and a heat of combustion of less than 19 KJ/kg. Class 3 (A3) refrigerants have flammability over this limit and this includes many hydrocarbons such as propane, which is otherwise a good refrigerant. There will be no need for additional flammability consideration because the disclosed formulation will be a direct drop in for R-454B in new applications as well as make up gas at lower flammability considerations as an A2L (lower flammability).

Drop-In Capability

In response to the global HFC phasedown, many of the largest air conditioning equipment manufacturers have redesigned their air conditioning equipment to utilize R-32 because of its lower GWP rating of 677. R-454B replaces R-32, which is a high-pressure, mildly flammable refrigerant (A2L). In 2029, the AIM Act will reduce HFC production and imports to 30% of baseline (70% reduction), and the market will require a supply of reclaimed refrigerants to make up for the shortfall needed to service the installed equipment base. R-454B has been specified as a drop-in replacement for R-32 and has a lower GWP of 466 compared to 675 for R-32. The 136 net GWP for EX1 of the disclosure represents 29% of the GWP of R-454B and 20% of the GWP of R-32, for which R-454B is a replacement. If recycled R-1234ZE can be obtained, the net GWP can be lowered even further.

R-454B is used primarily in home cooling applications like multi-family living and impacts nearly every person in the United States. Of the 3 classifications of flammability in AHRI R-32 receives a "mildly" flammable designation compared to the A1 "non-flammable" category of, for example, R-410A (combination of R-32 and R-125). The disclosed formulation will be a direct drop-in in existing applications as well as make up gas at lower flammability considerations.

The formulation EX1 of the disclosure matches, i.e., is identical to the performance of R-454B with a deviance of ±2%. The formulation of the disclosure has a theoretical boiling point of about −51° F.±1.02° F., a liquid phase pressure of about 221 psia±4.42 psia at 70° F., a vapor phase pressure of about 198 psia 9.90 psia at 70° F., has a liquid phase density of about 1.02 $g/cm^3$±0.2 $g/cm^3$ at 70° F., a vapor phase density of about 0.043 $g/cm^3$±8.6×$10^{-4}$ $g/cm^3$ at 70° F., a liquid phase enthalpy of about 0.236 KJ/g±4.72×$10^{-3}$ KJ/gat 70° F., a vapor phase enthalpy of about 0.480 KJ/g±9.6×$10^{-3}$ KJ/g at 70° F., a liquid phase entropy of about 6.2×$10^{-4}$ KJ/gR±1.24×$10^{-5}$ at 70° F., and a vapor phase entropy of about 1.1×$10^{-3}$ KJ/gR±2.2×$10^{-5}$ KJ/gR at 70° F.

The ±2% deviance also applies to the formulation of the disclosure itself. The formulation of the disclosure is thus about 72.8 wt %±2 wt % difluoromethane; about 7.2 wt %±2 wt % pentafluoroethane, about 2 wt %±2 wt % $CO_2$ (but greater than 0 wt %), and about 18 wt %±2 wt %1,3,3,3-tetrafluoropropene.

Lubricants

The formulations disclosed in this document can also include lubricants such as mineral oil, alkylbenzene oil, or polyol ester (POE) as an option.

In another embodiment, a synthetic polyol ester (POE) lubricant can be used. It is compatible for use in refrigeration and air-conditioning compressors using HFC refrigerants, as well as for original equipment manufacturing (OEM) retrofitting operations. The POE forms a single clear phase, meaning it is miscible with the disclosed formulations. This makes the lubricant more efficient as it can lower the viscosity of the lubricant in the system, allowing it to return to the compressor more easily. Unlike mineral oil lubricants, this composition is compatible with all types of compressors, including reciprocating and rotary compressors in residential air conditioning, and centrifugal, reciprocating and scroll compressors in industrial and commercial refrigeration and air conditioning.

The synthetic POE lubricant in this disclosure can be produced by combining neopentyl polyol, aliphatic monocarboxylic acid and a small amount of acid catalyst in a reaction zone. This creates a reaction mixture, with the neopentyl polyol being represented by the structural formula: The POE of the present disclosure can be obtained by introducing neopentyl polyol material, aliphatic monocarboxylic acid material and a catalytic quantity of acid catalyst material into a reaction zone, whereby a reaction mixture is formed, the neopentyl polyol material being at least one neopentyl polyol represented by the structural formula:

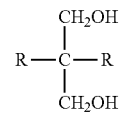

in which each R is independently selected from $-CH_3$, $-C_2H_5$ and $-CH_2OH$. The aliphatic monocarboxylic acid material is at least one aliphatic hydrocarbon monocarboxylic acid, and the acid catalyst material is at least one acid esterification catalyst, wherein the initial concentration of the aliphatic monocarboxylic acid material in the reaction mixture is such as to provide an initial mole ratio of carboxyl groups to hydroxyl groups in the reaction mixture of from about 0.25:1 to about 0.5:1, and, while the reaction mixture is established and maintained at about 338-392° F. (170-200° C.), aliphatic monocarboxylic acid vapor and water vapor are withdrawn from the reaction zone.

Another approach would be to produce a poly(neopentyl polyol) ester composition by (i) reacting a neopentyl polyol having the formula:

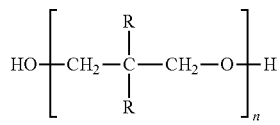

wherein each R is independently selected from $CH_3$, $C_2H_5$ and $CH_2OH$ and n is a number from 1 to 4, with at least one monocarboxylic acid having 2 to 15 carbon atoms in the presence of an acid catalyst and at an initial mole ratio of carboxyl groups to hydroxyl groups of greater than 0.5:1 to 0.95:1 to form a partially esterified poly(neopentyl polyol) composition; and (ii) reacting the partially esterified poly(neopentyl polyol) composition produced in (i) with additional monocarboxylic acid having 2 to 15 Carbon atoms to form a final poly(neopentyl polyol) ester composition.

The properties of the POE of the present disclosure can be in the viscosity range of about 20 to 68 cSt at 40° C. (104° F.) and about 3 to 7 cSt at 100° C. (212° F.). The viscosity index should be in the range of about 100 to 130. The pour point should be in the range of about -40 to -50° C. (-40 to -58° F.). The density at 20° C. (68° F.) should be in the range of about 0.97 to 0.98 g/ml. The flash point should be in the range of about 240 to 270° C. (about 464 to 518° F.). The acid value should be less than about 0.05 mg KOH/g.

The disclosure is not restricted to POE lubricant. Other lubricants can include mineral or hydrocarbon oil, alkylbenzene oil, white or paraffinic oil and mixtures thereof. The amount of lubricating oil is an amount effective in providing acceptable lubrication to the compressor parts for its longevity. An effective amount of these conventional lubricating oils is the amount recommended by the equipment manufacturer. Typically, the conventional lubricating oil is present in an amount from about 1 to about 60 wt %. The present disclosure has unexpectedly found the amount of POE to be less than about 1 wt %, as little as about 0.67 wt %, with even 0.4 wt % giving excellent lubrication. The range in which POE can be present can be from about 0.1 to about 5 wt %.

Additives

The compositions of the disclosure may contain one or more additives such as additives that enhance oxidation resistance and thermal stability, inhibitors of corrosion, deactivators of metals, lubricants, viscosity index enhancers, pour and/or floc point depressants, detergents, dispersants, antifoaming agents, anti-wear agents, UV dyes, sealants and extreme pressure resistant additives. Some of these additives have multiple functions, for example, certain additives may provide anti-wear and extreme pressure resistance properties, or act as both a metal deactivator and a corrosion inhibitor. However, the total amount of all additives should not exceed 8% by weight or, preferably, 5% by weight of the total composition.

The compositions of the disclosure may contain an effective amount of various additives such as antioxidants, corrosion inhibitors, metal deactivators, lubricity additives, viscosity index enhancers, pour and/or floc point depressants, detergents, dispersants, antifoaming agents, anti-wear agents, UV dyes, sealants, and extreme pressure resistant additives. The effective amount of each additive can vary, but generally ranges from 0.01 to 5% by weight for antioxidants, 0.01 to 5% by weight for corrosion inhibitors, 0.001 to 0.5% by weight for metal deactivators, 0.5 to 5% by weight for lubricity additives, 0.01 to 2% by weight for viscosity index enhancers and pour and/or floc point depressants, 0.1 to 5% by weight for detergents and dispersants, 0.001 to 0.1% by weight for antifoaming agents, and 0.1 to 2% by weight for anti-wear and extreme pressure resistance components. These percentages are based on the total composition. It's important to note that the amounts of additives may vary depending on the specific circumstances and a single molecular type or a mixture of types may be used for each type of additive component.

The compositions of the disclosure may include additives that enhance oxidation resistance and thermal stability, such as diphenyl-, dinaphthyl-, and phenylnaphthyl-amines, where the phenyl and naphthyl groups can be substituted, such as N,N'-diphenyl phenylenediamine, p-octyldiphenylamine, p,p-dioctyldiphenylamine, N-phenyl-1-naphthylamine, N-phenyl-2-naphthylamine, N-(p-dodecyl)phenyl-2-naphthylamine, di-1-naphthylamine, and di-2-naphthylamine, phenothiazines such as N-alkyl-phenothiazines, imino(bisbenzyl); hindered phenols such as 6-(t-butyl) phenol, 2,6-di-(t-butyl) phenol, 4-methyl-2,6-di-(t-butyl) phenol, 4,4'-methylenebis(2,6-di-{t-butyl}phenol); combinations of two or more thereof. These are only examples and not limiting.

The compositions of the disclosure may include cuprous metal deactivators, such as imidazole, benzimidazole, 2-mercaptobenzothiazole, 2,5-dimercaptothiadiazole, salicylidine-propylenediamine, pyrazole, benzotriazole, tolutriazole, 2-methylbenzimidazole, 3,5-dimethyl pyrazole, and methylene bis-benzotriazole. Benzotriazole derivatives are preferred. Other examples of metal deactivators and/or corrosion inhibitors that can be used include organic acids and their esters, metal salts, and anhydrides, such as N-oleyl-sarcosine, sorbitan mono-oleate, lead naphthenate, dodecenyl-succinic acid and its partial esters and amides, and 4-nonylphenoxy acetic acid; primary, secondary, and tertiary aliphatic and cycloaliphatic amines and amine salts of organic and inorganic acids, such as oil-soluble alkyl ammonium carboxylates; heterocyclic nitrogen containing compounds, such as thiadiazoles, substituted imidazolines, and oxazolines; quinolines, quinones, and anthraquinones; propyl gallate; barium dinonyl naphthalene sulfonate; ester and amide derivatives of alkenyl succinic anhydrides or acids, dithiocarbamates, dithiophosphates; amine salts of alkyl acid phosphates and their derivatives. These are only examples and not limiting.

Examples of lubricity additives that can be used include derivatives of fatty acids and natural oils with long chain molecules, such as esters, amines, amides, imidazolines, and borates.

Examples of additives that can be used to enhance the viscosity index include polyacrylates, polymethacrylates, copolymers of vinyl pyrrolidone, acrylates, methacrylates, polybutenes, and styrene-acrylate copolymers.

Examples of suitable pour point and/or floc point depressants include polymethacrylates such as methacrylate-ethylene-vinyl acetate terpolymers; alkylated naphthalene derivatives; and products of Friedel-Crafts catalyzed condensation of urea with naphthalene or phenols.

Examples of suitable detergents and/or dispersants include poly butenyl succinic acid amides; polybutenyl phosphonic acid derivatives; long chain alkyl substituted aromatic sulfonic acids and their salts; and metal salts of alkyl sulfides, of alkyl phenols, and of condensation products of alkyl phenols and aldehydes.

Examples of suitable antifoam agents include silicone polymers and acrylates.

Examples of suitable anti-wear and extreme pressure resistance agents include sulfurized fatty acids and fatty acid esters, such as sulfurized octyl tallate; sulfurized terpenes; sulfurized olefins; organopolysulfides; organophosphorus derivatives including amine phosphates, alkyl acid phosphates, dialkyl phosphates, anime dithiophosphates, trialkyl and triaryl phosphorothioates, trialkyl and triaryl phosphines, and dialkylphosphites, e.g., amine salts of phosphoric acid monoethyl ester, amine salts of dinonylnaphthalene sulfonate, triphenyl phosphate, trinaphthyl phosphate, diphenyl cresyl and cresyl diphenyl phosphates, naphthyl diphenyl phosphate, triphenyl phosphorothionate; dithiocarbamates, such as an antimony dialkyl dithiocarbamate; chlorinated and/or fluorinated hydrocarbons, and xanthates.

Fluorescent dyes may be added to the refrigerant mixture in order to detect leaks. One preferred leak detection or dye additive is a fluorescent, alkyl substituted perylene dye compound, dissolved in an oil which is the same as the system lubricating oil, or which is otherwise compatible with the refrigerant and oil. The dye may be soluble in polyhalogenated hydrocarbon refrigerants and fluoresces a brilliant yellow-green under illumination by long wave ultraviolet light. In an automobile air conditioner system that has a fully-charged capacity of thirty-three ounces of R-134A refrigerant (or a refrigerant blend) and seven ounces of lubricating oil, an amount of about 0.014 ounces dye additive is effective to locate leaks without adversely affecting the operation of the system.

In an embodiment, the dye is a fluorescent dye which is a solid compound or composition soluble in both the refrigerant and refrigeration or system lubricant. The dyes could be naphthoxanthene, perylene and naphthalene compounds, such as:

naphtho{3,2,1-kl}xanthene-2,8-dialkyl,
naphtho{3,2,1-kl}xanthene-2,8-dimethyl
3,9-perylene dialkyl acetate,
3,9-perylene dimethyl acetate,
4-alkylamino-n-alkyl-naphthalimide,
4-alkylamino-n-methyl-naphthalimide, and
dinaphtho(1,2,3-cd; 1'2'3-lm)perylene-9,18-dione, alkyl derivatives.

Dye concentrates can be used which includes a lubricant and at least about 3 weight percent of a leak detection dye, wherein the dye concentrate is a suspension or a semi-solid material, the dye concentrate has a viscosity of at least 10 cP at room temperature, the leak detection dye includes a naphthalimide, a perylene, a thioxanthene, a coumarin, or a fluorescein, and the leak detection dye includes a plurality of particles in which greater than 60 percent of the particles have a particle size of less than 40 microns.

Similar to the liquid dyes, the fluorescent solid dye must be stable at operating temperatures of the A/C or refrigeration system and should not change the properties of the refrigerant or the system lubricant or adversely affect components and parts of the system.

Sealants may also be added to the refrigerant mixture in order to seal leaks of refrigerant. Leaks allow refrigerants and other working fluids to escape into the atmosphere, contaminating the environment and decreasing the efficiency and cooling capacity of the unit. If large amounts of cooling working fluids such as refrigerants escape, the system may overheat and the service life of the unit will thereby be shortened. Further, the unit may suffer mechanical failure from the loss of the working fluid. In general, leaks in heating and cooling systems also decrease the heat transfer efficiency of these systems.

One example of a sealant is a composition of about 60% by volume of vinyltrimethoxysilane, about 30% by volume of n-beta(aminoethyl)-gamma-aminopropyltrimethoxysilane; and about 10% by volume of methyltrimethoxysilane, a water scavenger. The methyltriethoxysilane is a water scavenger and the vinyl trimethylsilane is a metal bonding material in which the n-beta-(aminoethyl)-gamma-aminopropyltrimethoxysilane is for cross linking.

An organosilane or components of the sealant mixture may include components that can be represented as $(R_1)(R_2)Si(R_3)(R_4)$ where, $R_1$ is an alkyl radical of 1-4 carbon atoms or vinyl or —OH, $R_2$ is $R_1$ or —$OR_1$ or —$NH(R_1)$ or —$N(R_1)_2$ or —$R_1NHR_1NH_2$, $R_3$ is $R_1$ or —$OR_1$ or —$NH(R_1)$ or —$N(R_1)_2$ or —$R_1NHR_1NH_2$, and $R_4$ is $R_1$ or —$OR_1$ or —$NH(R_1)$ or —$N(R_1)_2$ or —$R_1NHR_1NH_2$.

A component of the sealant mixture may include components that can be represented as $(R_5)(R_6)(R)Si$—O—$Si(R_5)(R_6)(R_7)$ $R_5$, $R_6$ or $R_7$ are each any one of $R_1$, $R_2$, $R_3$ or $R_4$ where, $R_1$ is an alkyl radical of 1-4 carbon atoms or vinyl or —OH, $R_2$ is $R_1$ or —$OR_1$ or —$NH(R_1)$ or —$N(R_1)_2$ or —$R_1NHR_1NH_2$, $R_3$ is $R_1$ or —$OR_1$ or —$NH(R_1)$ or —$N(R_1)_2$ or —$R_1NH R_1NH_2$, and $R_4$ is $R_1$ or —$OR_1$ or —$NH(R_1)$ or —$N(R_1)_2$ or —$R_1NHRR_1NH_2$.

Other components which can be included are oligomers of the monomeric silanes described. One such example are the siloxanes: $(R_5)(R_6)(R_7)Si$—O—$Si(R_5)(R_6)(R_7)$ Where $R_5$, $R_6$ or $R_7$ may be $R_1$, $R_2$, $R_3$ or $R_4$.

The sealant mixture may also include a lubricant miscible with the organosilane and refrigerant for use in the system. The miscible mixture may include a lubricant selected from one or more of a polyol ester, polyalkylene glycol, mineral oil, polyalphaolefin and alkylbenzene. The miscible mixture may include a lubricant further formed from additives to enhance and refresh the performance of the lubricant in the compressor.

When selecting an organosilane, several factors are considered. The organosilane is chosen to be miscible in the lubricant fluid. It is typically a monomer, but may contain oligomers that can form a solid polymer with itself or other chosen organosilanes when exposed to moisture under the conditions of the specific application. The reaction rate of the organosilane or mixture of organosilanes must be fast enough to create an effective seal at the site of the leak. The polymeric seal must be strong enough to prevent further leakage of refrigerant from the system. In addition, the organosilanes should be stable when not exposed to moisture, non-corrosive, and not harmful to the components of the system or the environment. The amount and type of organosilanes used should not interfere with the normal operation of the refrigerant fluid, such as its vaporization and liquefaction characteristics.

An effective amount of the foregoing additive types is generally in the range from about 0.01 to about 5 wt % for the antioxidant component, about 0.01 to about 5 wt % for the corrosion inhibitor component, from about 0.001 to about 0.5 wt % for the metal deactivator component, from about 0.5 to about 5 wt % for the lubricity additives, from about 0.01 to about 2 wt % for each of the viscosity index enhancers and pour and/or floc point depressants, from about 0.1 to about 5 wt % for each of the detergents and dispersants, from about 0.001 to about 0.1 wt % for antifoam agents, and from about 0.1 to about 2 wt % for each of the anti-wear and extreme pressure resistance components. All these percentages are by weight and are based on the total composition. It is to be understood that more or less than the stated amounts of additives may be more suitable to particular circumstances, and that a single molecular type or a mixture of types may be used for each type of additive component. As used herein, the term "effective amount" means the amount of each component which upon combination with the other component or components, results in the formation of the present compositions.

Many of the aforementioned additives are multifunctional. For example, certain additives may impart both anti-wear and extreme pressure resistance properties, or function both as a metal deactivator and a corrosion inhibitor. Cumulatively, all additives preferably do not exceed about 8% by weight, or more preferably do not exceed about 5% by weight, of the total composition.

Government Mandates and Refrigerant Reduction

FIGS. 11 and 11A are a reclamation summary of data by the U.S. EPA for reclamation data of ODS (ozone-depleting substances) as well as HFCs. In addition, you can see the category of the growing quantities of HFCs that are classified as "mixed". This is a growing environmental category with no known uses. In looking at all of the data, a few thoughts can be clearly seen:

FIGS. 11 and 11A are a summary of reclamation data by the U.S. EPA for ozone-depleting substances (ODS) and hydrofluorocarbons (HFCs). The data also shows the increasing amount of HFCs classified as "mixed" which have no known uses and is a growing environmental concern. By analyzing the data, a few observations can be made.

As shown in FIG. 11A, in 2020, 2.4 MM pounds of R410A of the total sold into the market were reclaimed.

The most difficult stream that exists is the category of "mixed" refrigerant that as the EPA explains is a combination of ODS (R-22) and various HFC streams that cannot be reprocessed and represents nearly 1 million pounds per year, but it is being stockpiled because of complexity.

From a mass balance perspective, it is clear from all data presented that reclamation of refrigerants is severely lacking with the majority of refrigerants vented back into the atmosphere and contributing to global warming.

Manufacturers of next-generation HFC/HFO blends do not participate in reclamation and instead focus on selling new materials with lower GWP back into the market, without managing the lifecycle of the refrigerants that have already been sold.

Manufacture and Use

The refrigerant composition of the present disclosure can be used as an original OEM refrigerant or as a drop-in replacement for equipment using R-454B.

Figure 15:
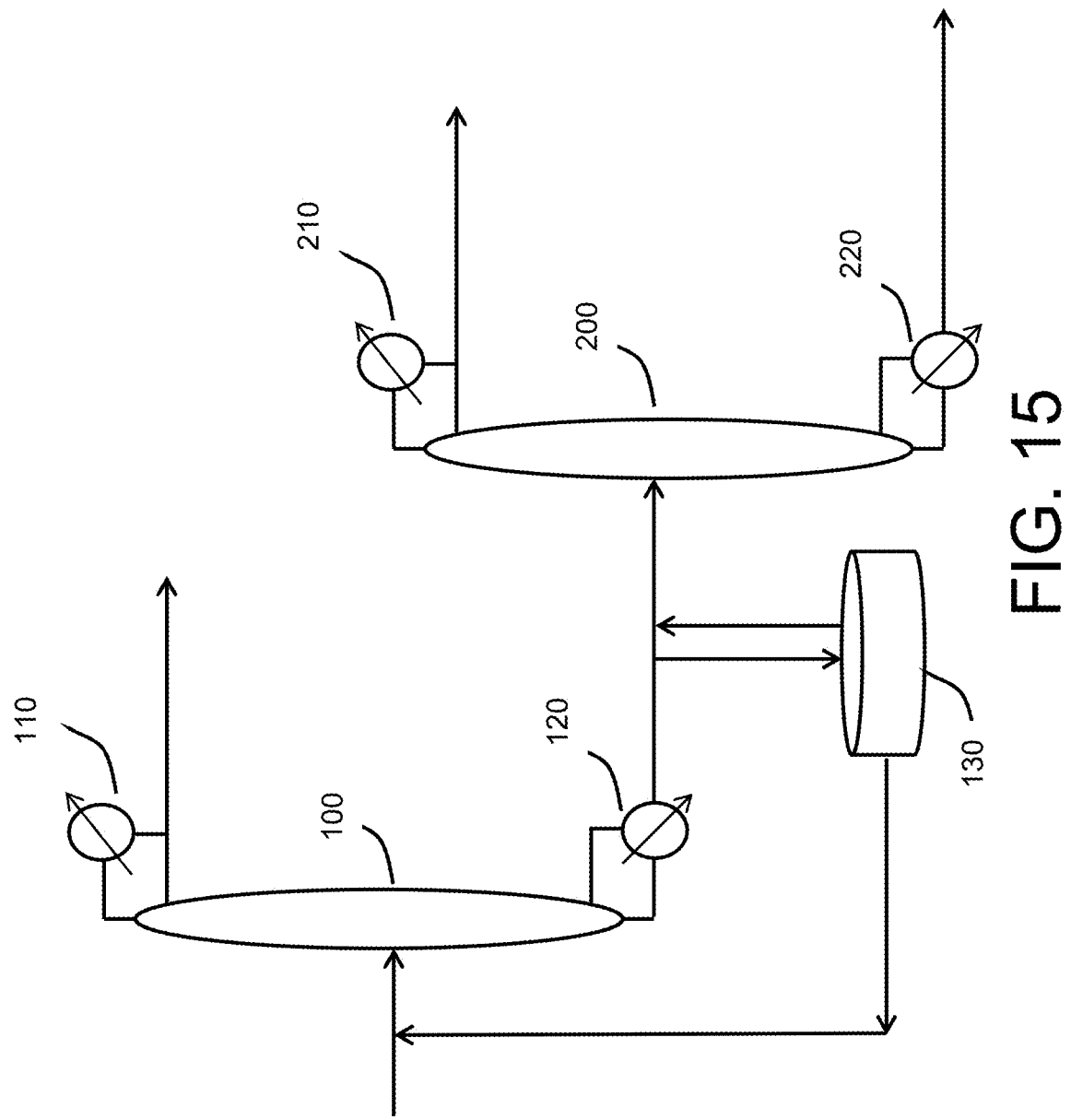
FIG. 15 is a schematic diagram of a distillation apparatus according to an embodiment of the disclosure.

FIG. 15 is a schematic diagram of a distillation apparatus configured to produce an R-32:R-125 mixture that can be utilized as a 0 net GWP component for a drop-in replacement for R-454B.

FIG. 15 illustrates a process in which a reclaimed refrigerant mixture is injected into the center of a distillation column 100. The column 100 is equipped with a reflux condenser 110 and a reboiler 120. The column 100 is packed with a material, such as steel Pall rings, that provides enough theoretical plates. The lighter fraction is distilled from the top of column 100, while the heavier fraction is drained from the bottom and stored in storage tank 130 until it can be distilled again in column 100.

Alternatively, the heavier fraction can be distilled in an optional second column 200, which is equipped with a reflux condenser 210 and a reboiler 220. This optional second column 200 allows for distillation of the refrigerant mixture in either batch or continuous modes. FIG. 14 does not show temperature sensors, pressure sensors, pressure regulators, temperature regulators, mass flow controllers, process control hardware, process control software and other process details which are known in the art.

There are various streams of reclaimed materials that can be used in the distillation process outlined in the disclosure. Many of these reclaimed materials are consolidated by contractors and are collected from gas stations, HVAC shops and other small businesses where little or no effort is made to separate different types of refrigerants, including HFCs and ODS materials. Some of the more common reclaimed streams are listed in Table 5.

TABLE 5

Reclaimed Mixed Materials.

| Components | Feed 0 (wt %) | Feed 1 (wt %) | Feed 2 (wt %) | Feed 3 (wt %) | Feed 4 (wt %) |
|---|---|---|---|---|---|
| R-134A | 15.5 | 1.20 | 2.50 | 7.50 | 11.0 |
| R-125 | 12.5 | 5.00 | 5.00 | 11.0 | 21.5 |
| R-32 | 12.5 | 5.00 | 5.00 | 11.0 | 21.5 |
| R-143A | 6.50 | 1.30 | 0.00 | 5.50 | 13.0 |
| R-22 | 50.0 | 87.5 | 87.5 | 65.0 | 33.0 |
| HC | 3.00 | 0.00 | 0.00 | 0.00 | 0.00 |
| $H_2O$ | $5 \times 10^{-5}$ | $5 \times 10^{-6}$ | $5 \times 10^{-6}$ | $5 \times 10^{-5}$ | $5 \times 10^{-5}$ |
| Total | 100 | 100 | 100 | 100 | 100 |

The following observations can be made regarding the reclaimed mixed materials set forth in Table 5:
- R-22 is the most common ODS (ozone depleting substance) because many replacement HFC products have been improperly put into systems "topping off" with HFC blends.
- Feed 0 represents the most likely and worst-case scenario for much of the mixed refrigerant in the U.S. market with high content of R-143a that has a boiling point very similar to R-22 and is difficult to manage in the fractionation process.
- Highly flammable substances like butane, Isobutane and propane have been used as lubricants in a variety of refrigerant applications to replace R-22. Dealing with class 3 flammables is critical.
- Mixed materials in many cases contain R-143A (from R-404A) that is mixed at the contractor level, making fractionation very difficult and requiring unique technical solutions in fractionation and forcing the high purity R-32:R-125 mix in order to extract the components.

The distillation column(s) of the disclosure have been designed using the process simulation software package, ASPEN, and then verified by Koch-Glitsch. ASPEN is widely used in industry to predict the performance of a process using mathematical models based on the process design and the selection of thermodynamic models. The process of the disclosure can produce the 91:9 R-32:R-125 material directly from a single first pass, utilizing waste streams of material that would otherwise be vented or stored around the country or ultimately burned in a rotary kiln with $CO_2$. The 91:9 R-32:R-125 material, which has a zero net GWP, can be used to formulate a drop-in replacement for R-454B.

Example 1—Feed 0

Feed Zero is fed into the center of the distillation column at a temperature about 140-150° F. and a pressure of about 400-420 psia. The top fraction is taken off at a temperature of about 95-105° F. and about 370-380 psia. The bottom fraction is taken off at a temperature of about 140-150° F. and a pressure of about 375-385 psia. The composition of the top and bottom fractions is shown in Table 6.

TABLE 6

Top and Bottom Fractions of Feed-0 Case (wt %).

| Component | Top Fraction (wt %) | Bottom Fraction (wt %) |
|---|---|---|
| R-32 | 91.3 | 6.95 |
| R-125 | 8.5 | 12.8 |
| R-143 | 0.264 | 6.93 |
| R-22 | $4.93 \times 10^{-7}$ | 53.5 |
| R-134 | $6.23 \times 10^{-11}$ | 16.6 |
| Oils | $2.11 \times 10^{-17}$ | 3.21 |
| Water | $1.95 \times 10^{-27}$ | $5.32 \times 10^{-7}$ |

With the system of the disclosure and considering high volumes of R-143 in the feedstock, a final product of about 91% R-32, about 9% R-125 that has zero moisture can be formulated into a low net GWP drop-in replacement for R-454B, or packaged and sold directly into new equipment as a net zero GWP replacement for R-32.

Example 2.—Feed 1

Feed 1 is fed into the center of the distillation column at a temperature of about 145-155° F. and a pressure of about 400-420 psia. The top fraction is taken off at a temperature of about 95-105° F. and about 370-380 psia. The bottom fraction is taken off at a temperature of about 140-150° F. and a pressure of about 375-385 psia. The composition of the top and bottom fractions is shown in Table 7.

TABLE 7

Top and Bottom Fractions of Feed-1 Case (wt %).

| Component | Top Fraction (wt %) | Bottom Fraction (wt %) |
|---|---|---|
| R-32 | 65.3 | 0.0392 |
| R-125 | 33.6 | 2.65 |
| R-143 | 0.726 | 1.35 |
| R-22 | 0.375 | 94.7 |
| R-134 | $2.30 \times 10^{-6}$ | 1.30 |
| Oils | 0 | 0 |
| Water | $9.03 \times 10^{-19}$ | $5.41 \times 10^{-4}$ |

In this case, the top fraction yields a ratio of about 65:35 R-32:R-125, given a variation of from about ±1% up to about ±2%. The minor amounts of other components are also acceptable since they also have a net 0 GWP. Further distillation steps can further isolate components, including an 0.9998 fraction of R-22 that can be used in R-22 compatible equipment with a net GWP of zero. However, using this fraction to manufacture a drop-in replacement for R-454B is problematic because additional material may have to be added to obtain the optimal ratio of R-32 to R-25.

This Feed 1 is a very common mixed ODS feed stream, but difficult to process. With the columns and considering high volumes of R-143a in the feedstock the disclosure obtains a final product of 65% R-32 and 35% R-125 that has >99.5% purity, zero moisture and can be packaged and sold directly into new equipment and as a replacement for R410A. Likewise, the technology can handle nearly all legacy mixed streams, and the product of the disclosure can be adapted to replace all past refrigerants into new equipment. However, this feed may be difficult to use as the basis of a formulation for a drop-in replacement for R-454B.

Example 3.—Feed 2

Feed 2 is fed into the center of the distillation column at a temperature of about 145-155° F. and a pressure of about 400-420 psia. The top fraction is taken off at a temperature of about 95-105° F. and about 370-380 psia. The bottom fraction is taken off at a temperature of about 140-150° F. and a pressure of about 375-385 psia. The composition of the top and bottom fractions is shown in Table 8.

TABLE 8

Top and Bottom Fractions of Feed-2 Case (wt %).

| Component | Top Fraction (wt %) | Bottom Fraction (wt %) |
|---|---|---|
| R-32 | 65.4 | 0.0385 |
| R-125 | 34.3 | 2.59 |
| R-143 | 0 | 0 |
| R-22 | 0.335 | 94.7 |
| R-134 | $4.15 \times 10^{-6}$ | 2.71 |
| Oils | 0 | 0 |
| Water | $6.71 \times 10^{-19}$ | $5.41 \times 10^{-4}$ |

In this case, the top fraction yields a ratio of about 65:35 R-32:R-125, given a variation of about ±1% to about ±2%. The minor amount of other components is also acceptable, since they are all used as drop-ins for R-22. Further distillation steps can further isolate components, including an 0.9998 fraction of R-22 that can be used in R-22 compatible equipment with a net GWP of zero. Further distillation steps can further isolate components, including purified fractions of R-22 and R-134A. However, this feed may be difficult to use as the basis of a formulation for a drop-in replacement for R-454B.

Feed 2 is another mixture of ODS and HFC's that can be fractionated off of the column and turned into a finished product Example 4.—Feed 3

Feed 3 is fed into the center of the distillation column at a temperature about 140-150° F. and a pressure of about 400-420 psia. The top fraction is taken off at a temperature of 95-105° F. and about 370-380 psia. The bottom fraction is taken off at a temperature of about 135-145° F. and a pressure of about 375-385 psia. The composition of the top and bottom fractions is shown in Table 9.

TABLE 9

Top and Bottom Fractions of Feed-3 Case (wt %).

| Component | Top Fraction (wt %) | Bottom Fraction (wt %) |
|---|---|---|
| R-32 | 91.0 | 5.40 |
| R-125 | 8.7 | 11.2 |
| R-143 | 0.248 | 5.87 |
| R-22 | $6.95 \times 10^{-3}$ | 69.5 |
| R-134 | $3.26 \times 10^{-7}$ | 8.02 |
| Oils | 0 | 0 |
| Water | $2.28 \times 10^{-23}$ | $5.35 \times 10^{-3}$ |

With the system of the disclosure, a final product of about 91% R-32, about 9% R-125 that has zero moisture which can be used as a 0 net GWP component of a low GWP formulation of a drop-in replacement for R-454B, or can be packaged and sold directly into new equipment as a replacement for R-32. However, the top fraction is not suitable as a drop-in replacement for R-410A. The bottom fraction can be subjected to further distillation steps to obtain nearly pure R-22 and R-134 that can be used in R-22 and R-134 compatible equipment with a net GWP of zero.

Example 5—Feed 4

Feed 4 is fed into the center of the distillation column at a temperature of about 130-140° F. and a pressure of about 400-420 psia. The top fraction is taken off at a temperature of about 95-105° F. and about 370-380 psia. The bottom fraction is taken off at a temperature of about 140-150° F. and a pressure of about 375-385 psia. The composition of the top and bottom fractions is shown in Table 10.

TABLE 10

Top and Bottom Fractions of Feed-4 Case (wt %).

| Component | Top Fraction (wt %) | Bottom Fraction (wt %) |
|---|---|---|
| R-32 | 49.8 | 0.0226 |
| R-125 | 42.2 | 5.75 |
| R-143 | 7.61 | 17.1 |
| R-22 | 0.381 | 57.8 |
| R-134 | $4.28 \times 10^{-5}$ | 19.4 |
| Oils | 0 | 0 |
| Water | $1.32 \times 10^{-16}$ | $8.80 \times 10^{-4}$ |

In this case, the top fraction yields a ratio of about 5:4 R-32:R-125, which is not suitable as a direct replacement for R-454B or R-32. Further distillation steps can further isolate components, including purified fractions of R-22 and R-134A. Certain ODS mixed streams like Feed 4 are better to be utilized, for example, into a blended refrigerant replacement than as a pure replacement to optimize energy signature.

The process of charging a refrigeration or air conditioning system with the R-454B replacement is done using a cylinder that is designed to dispense a specific amount of refrigerant by weight. The pressure in the system is adjusted to match the pressure in the cylinder by reading the gauge and using a calibrated chart. To add more refrigerant to the system, heat is applied to the cylinder. In an example, a 25 or 30 lb cylinder is used that is filled with the refrigerant composition of the current disclosure and has an outlet compatible with R-32. This cylinder is then connected to the recharging manifold of the system to be charged.

Accordingly, the disclosure has shown that a drop-in replacement for R-454B unexpectedly produces a dramatic drop in net GWP while not sacrificing performance in air conditioning or refrigeration systems. Every pound of the 91:9 R-32:R-125 material used as a component for a replacement for R-454B represents a pound of R-454B that is not manufactured, thus reducing the 466 GWP associated with newly manufactured R-454B. The result is to reduce or prevent anthropogenic further emissions of greenhouse gases, in the framework of the Kyoto Protocol and the Paris Agreement. The technology of the disclosure will thus assist in the decarbonization of the atmosphere.

Throughout the specification and the embodiments, the following terms take at least the meanings explicitly associated herein, unless the context clearly dictates otherwise. Relational terms such as "first" and "second," and the like may be used solely to distinguish one entity or action from another entity or action without necessarily requiring or implying any actual such relationship or order between such entities or actions. The term "or" is intended to mean an inclusive "or" unless specified otherwise or clear from the context to be directed to an exclusive form. Further, the terms "a," "an," and "the" are intended to mean one or more unless specified otherwise or clear from the context to be directed to a singular form. The term "include" and its various forms are intended to mean including but not limited to. References to "one embodiment," "an embodiment," "example embodiment," "various embodiments," and other like terms indicate that the embodiments of the disclosed technology so described may include a particular function, feature, structure, or characteristic, but not every embodiment necessarily includes the particular function, feature, structure, or characteristic. Further, repeated use of the phrase "in one embodiment" does not necessarily refer to the same embodiment, although it may. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. A device or structure that is "configured" in a certain way is configured in at least that way, but may also be configured in ways that are not listed.

What is claimed is:

1. A method of preparing a refrigerant composition, comprising:

injecting a mixture of reclaimed refrigerants into a center of a distillation column, the mixture of reclaimed refrigerants comprising reclaimed difluoromethane, reclaimed pentafluoroethane and reclaimed chlorodifluoromethane;

removing from a top of the distillation column a refrigerant mixture of about 90-92 wt % of the reclaimed difluoromethane and about 8-10 wt % of the reclaimed pentafluoroethane;

removing the reclaimed chlorodifluoromethane from a bottom of the distillation column; and manufacturing the refrigerant composition from the refrigerant mixture removed from the top of the distillation column, wherein the refrigerant composition comprises:

about 72-74 wt % difluoromethane;

about 7-8 wt % pentafluoroethane, about 1-3 wt % $CO_2$, and about 17-19 wt % 1, 3, 3, 3-tetrafluoropropene.

2. The method of claim 1, wherein injecting the mixture of reclaimed refrigerants into the center of a distillation column is performed at a temperature of about 140-150° F. at a pressure of about 400-420 psia.

3. The method of claim 1, wherein removing from the top of the distillation column is performed at about 95-105° F. at a pressure of about 370-380 psia.

4. The method of claim 1, wherein removing from the bottom of the distillation column is performed at about 140-150° F. at a pressure of about 375-385 psia.

5. The method of claim 1, wherein the refrigerant composition comprises:

about 72.8 wt % difluoromethane;

about 7.2 wt % pentafluoroethane, about 2 wt % $CO_2$, and about 18 wt % 1, 3, 3, 3-tetrafluoropropene.

6. The method of claim 1, wherein the refrigerant composition has properties approximating a mixture of 68.9 wt % difluoromethane and 31.1 wt % 2, 3, 3, 3-tetrafluoropropene.

7. The method of claim 1, wherein the refrigerant composition has a net global warming potential about 29% of that of a mixture of about 68.9 wt % difluoromethane and 31.1 wt % 2, 3, 3, 3-tetrafluoropropene.

8. The method of claim 1, wherein the refrigerant composition has a theoretical boiling point of about −51° F.

9. The method of claim 1, wherein the refrigerant composition has a liquid phase pressure of about 221 psia at 70° F. and a vapor phase pressure of about 198 psia at 70° F.

10. The method of claim 1, wherein the refrigerant composition has a liquid phase density of about 1.02 g/cm$^3$ at 70° F. and a vapor phase density of about 0.043 g/cm$^3$ at 70° F.

11. The method of claim 1, wherein the refrigerant composition has a liquid phase enthalpy of about 0.236 KJ/g at 70° F. and a vapor phase enthalpy of about 0.480 KJ/g at 70° F.

12. The method of claim 1, wherein the refrigerant composition has a liquid phase entropy of about $6.2 \times 10^{-4}$ KJ/gR at 70° F.

13. The method of claim 1, wherein the refrigerant composition has a vapor phase entropy of about $1.1 \times 10^{-3}$ KJ/gR at 70° F.

14. The method of claim 1, wherein the refrigerant composition further comprises about 0.01-5 wt % lubricant.

15. The method of claim 14, wherein the lubricant is selected from the group consisting of mineral oil, alkylbenzene oil and polyol ester.

16. The method of claim 14, wherein the lubricant is an ester of at least one neopentyl polyol represented by the structural formula:

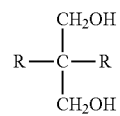

in which each R is independently selected from CH$_3$, C$_2$H$_5$ or CH$_2$OH.

17. The method of claim 14, wherein the refrigerant mixture further comprises at least one of an ultraviolet dye or a sealant.

18. The method of claim 1, wherein the refrigerant mixture comprises about 91 wt % difluoromethane and about 9 wt % pentafluoroethane.

19. The method of claim 1, wherein the refrigerant mixture contains less than $1.0 \times 10^{-18}$ wt % H$_2$O.

* * * * *